(12) United States Patent  
Shipe

(10) Patent No.: US 10,758,422 B1  
(45) Date of Patent: Sep. 1, 2020

(54) MEDICAL DRESSING SYSTEMS

(75) Inventor: Kim L. Shipe, Mesa, AZ (US)

(73) Assignee: FIELD TO FIELD, INC., Litchfield, IL (US)

(*) Notice: Subject to any disclaimer, the term of this patent is extended or adjusted under 35 U.S.C. 154(b) by 0 days.

(21) Appl. No.: 13/429,182

(22) Filed: Mar. 23, 2012

Related U.S. Application Data

(60) Provisional application No. 61/470,377, filed on Mar. 31, 2011, provisional application No. 61/505,056, filed on Jul. 6, 2011.

(51) Int. Cl.
*A61F 13/00* (2006.01)

(52) U.S. Cl.
CPC ................... *A61F 13/00* (2013.01)

(58) Field of Classification Search
USPC .............. 602/41–43, 48, 53, 56, 75, 79; 604/304–308
See application file for complete search history.

(56) References Cited

U.S. PATENT DOCUMENTS

| | | | |
|---|---|---|---|
| 370,055 A | 9/1887 | Haley | |
| 3,529,601 A * | 9/1970 | Kirkland | A61F 5/03 604/312 |
| 5,086,763 A | 2/1992 | Hathman | |
| 5,133,340 A | 7/1992 | Koopmann | |
| 5,158,541 A | 10/1992 | McCurley | |
| 5,229,191 A * | 7/1993 | Austin | D04H 3/14 128/849 |
| 5,429,593 A | 7/1995 | Matory | |
| 5,527,270 A | 6/1996 | Chase et al. | |
| 5,609,569 A | 3/1997 | Offenhartz | |
| 5,968,003 A | 10/1999 | Sisson | |
| 6,346,654 B1 * | 2/2002 | Snyder | A61F 13/0203 602/41 |
| 6,599,262 B1 | 7/2003 | Masini | |
| 6,653,520 B1 | 11/2003 | Mouton | |
| 7,131,400 B2 | 11/2006 | Wanveer et al. | |
| 7,241,627 B2 * | 7/2007 | Wilhelm | A61F 13/42 422/400 |
| 7,622,629 B2 | 11/2009 | Aali | |
| 7,652,190 B2 | 1/2010 | Johnson | |
| 7,658,719 B2 | 2/2010 | Bockol et al. | |
| 7,850,508 B2 | 12/2010 | Pitarelli | |
| 7,854,020 B2 | 12/2010 | Ehrlickman | |
| 2002/0099318 A1 * | 7/2002 | Suehr | A61F 13/0273 602/76 |
| 2004/0133143 A1 * | 7/2004 | Burton et al. | 602/58 |
| 2005/0004501 A1 | 1/2005 | Lorenzo | |

(Continued)

FOREIGN PATENT DOCUMENTS

WO    2010/120470 A1    10/2010

OTHER PUBLICATIONS

Department of the Army Field Manual FM 8-50: Bandaging and Splinting; Jun. 1957.*

(Continued)

*Primary Examiner* — Rachael E Bredefeld
*Assistant Examiner* — Caitlin A Carreiro
(74) *Attorney, Agent, or Firm* — Wenderoth, Lind & Ponack, L.L.P.

(57) ABSTRACT

A bandaging system relating to assisting improved wound compression, wound stability, and wound-management of wound sites and other wound care.

21 Claims, 9 Drawing Sheets

(56) References Cited

U.S. PATENT DOCUMENTS

| | | | |
|---|---|---|---|
| 2006/0188486 A1* | 8/2006 | Carpenter | A61L 15/26 424/93.7 |
| 2007/0042024 A1* | 2/2007 | Gladman | A61F 13/0273 424/445 |
| 2007/0083140 A1* | 4/2007 | Lohrer | A61F 5/0111 602/60 |
| 2008/0045876 A1* | 2/2008 | McVicker | 602/76 |
| 2008/0312572 A1* | 12/2008 | Riesinger | A61F 13/00008 602/43 |
| 2008/0312615 A1 | 12/2008 | Hunter | |

OTHER PUBLICATIONS

"Definition_unitary.PDF"; definition of "unitary"; accessed from www.google.com; Nov. 30, 2015.*

* cited by examiner

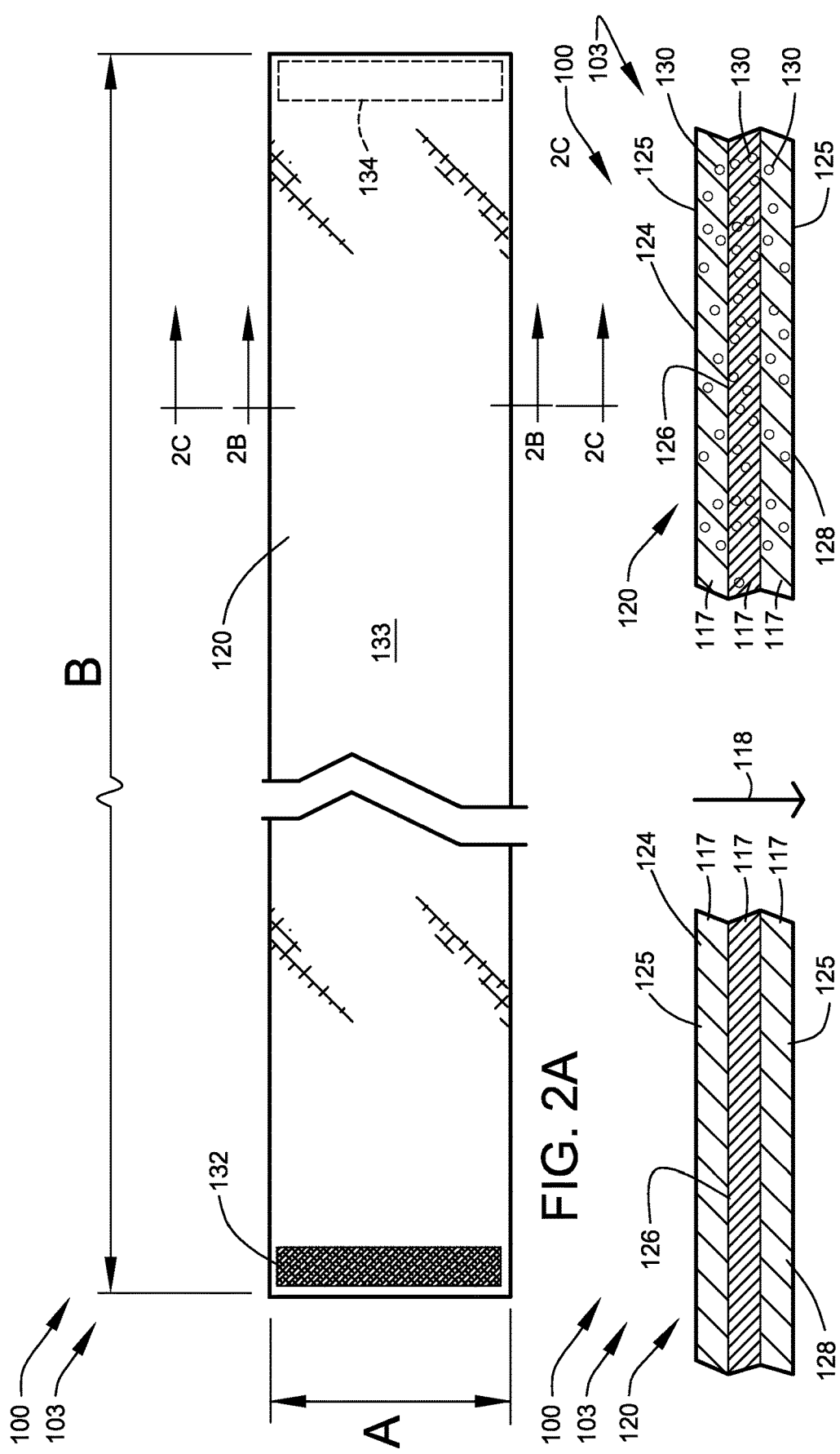

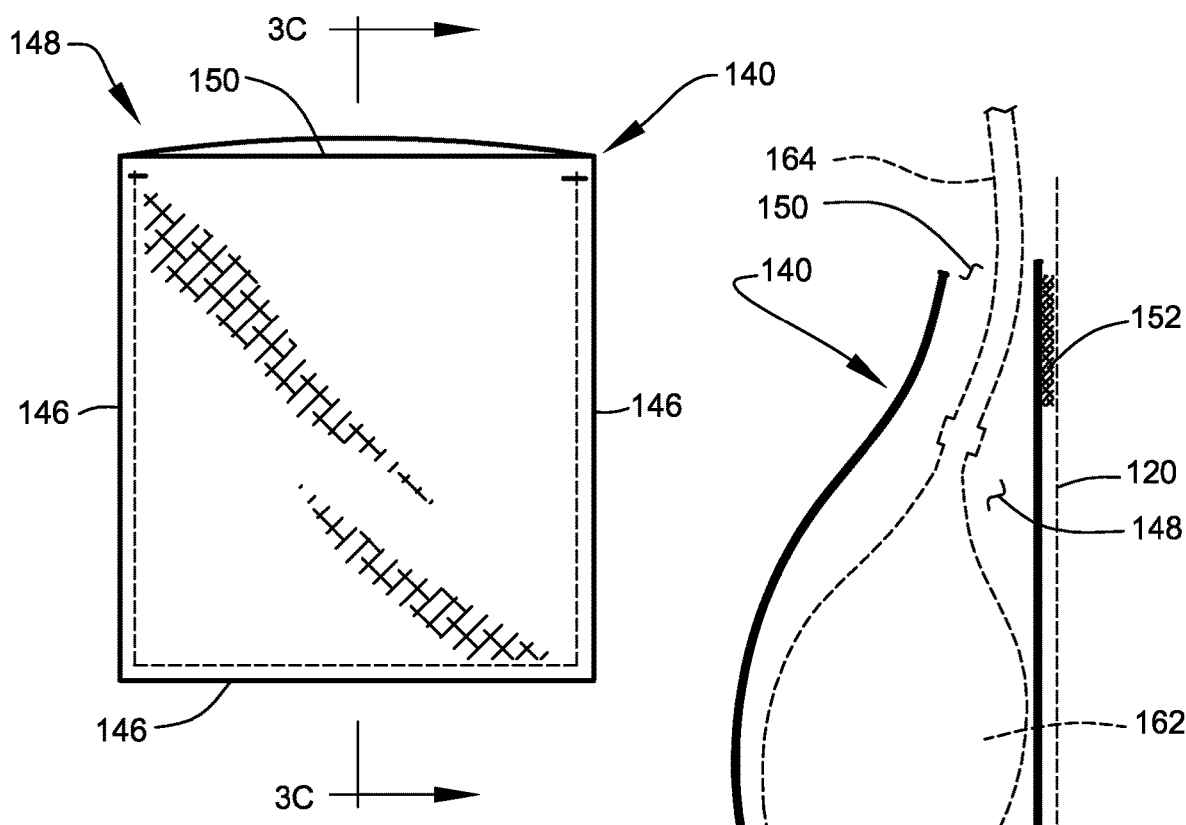
FIG. 3A
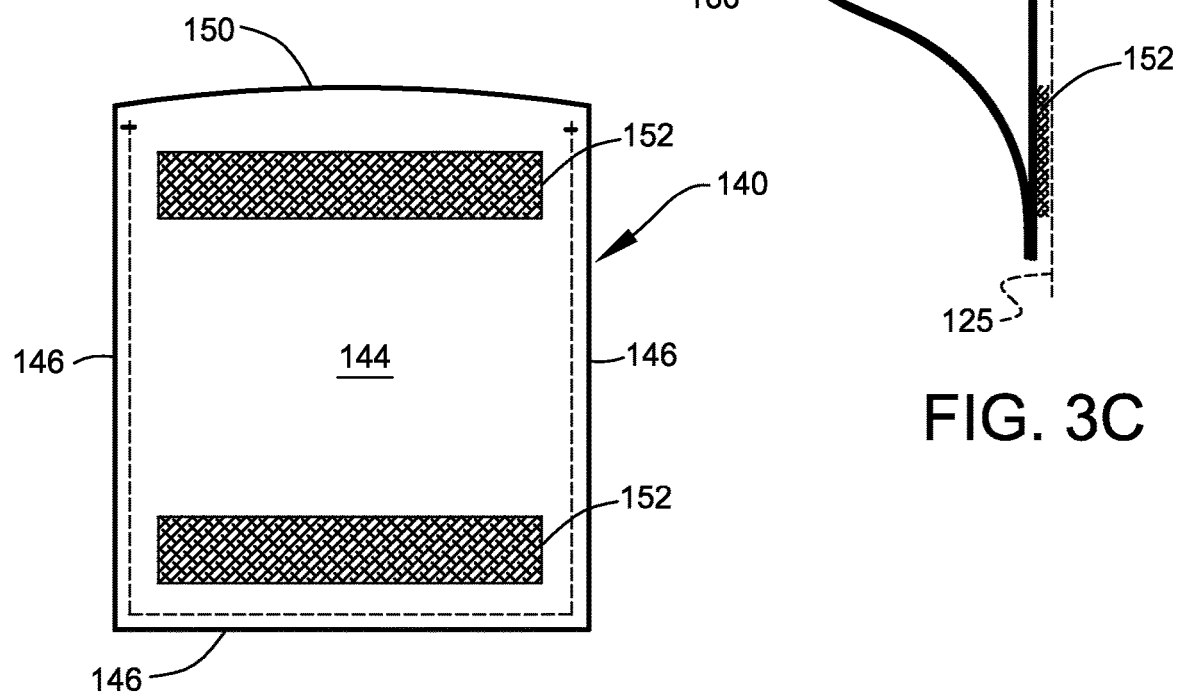
FIG. 3B
FIG. 3C

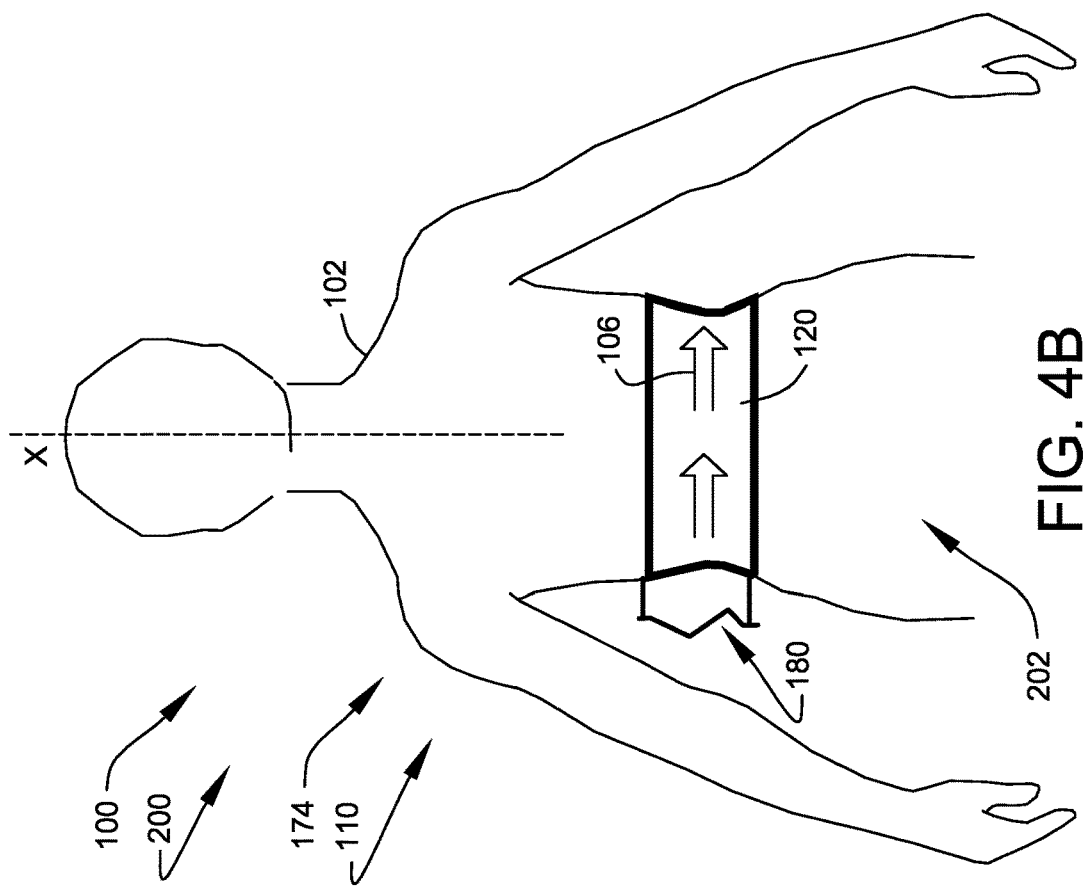
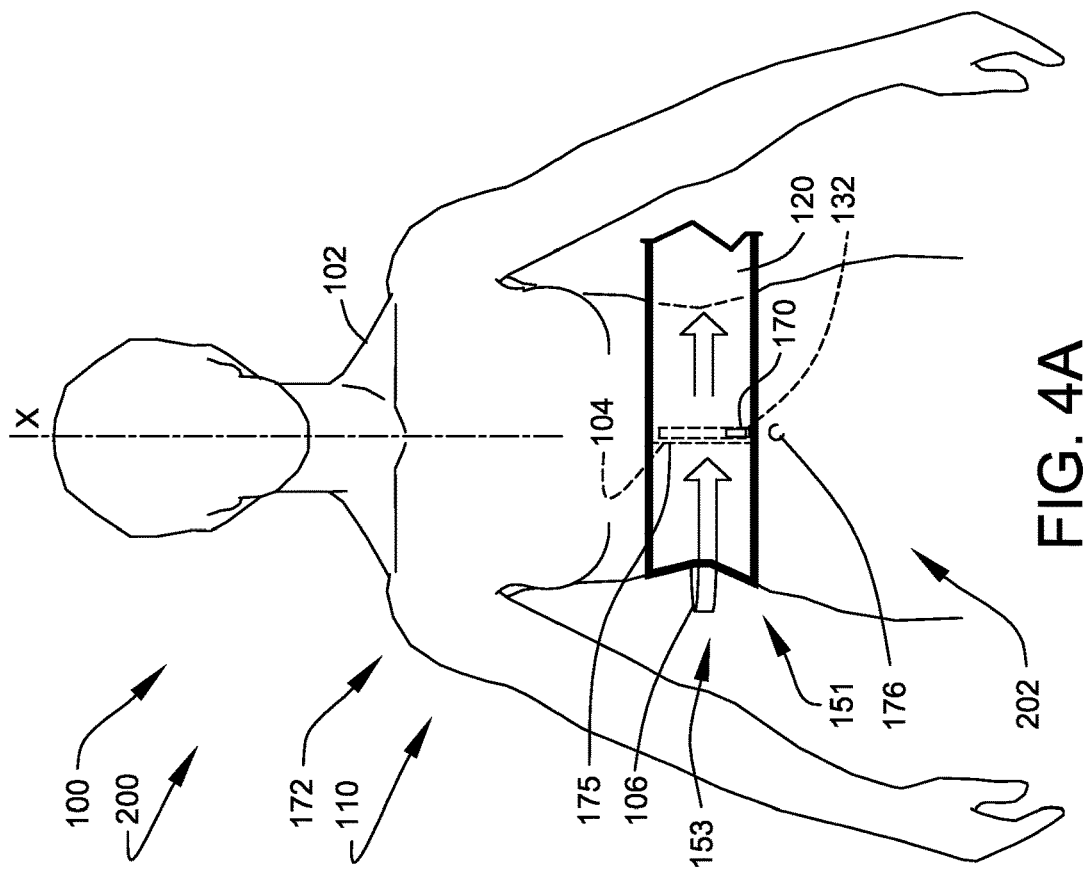

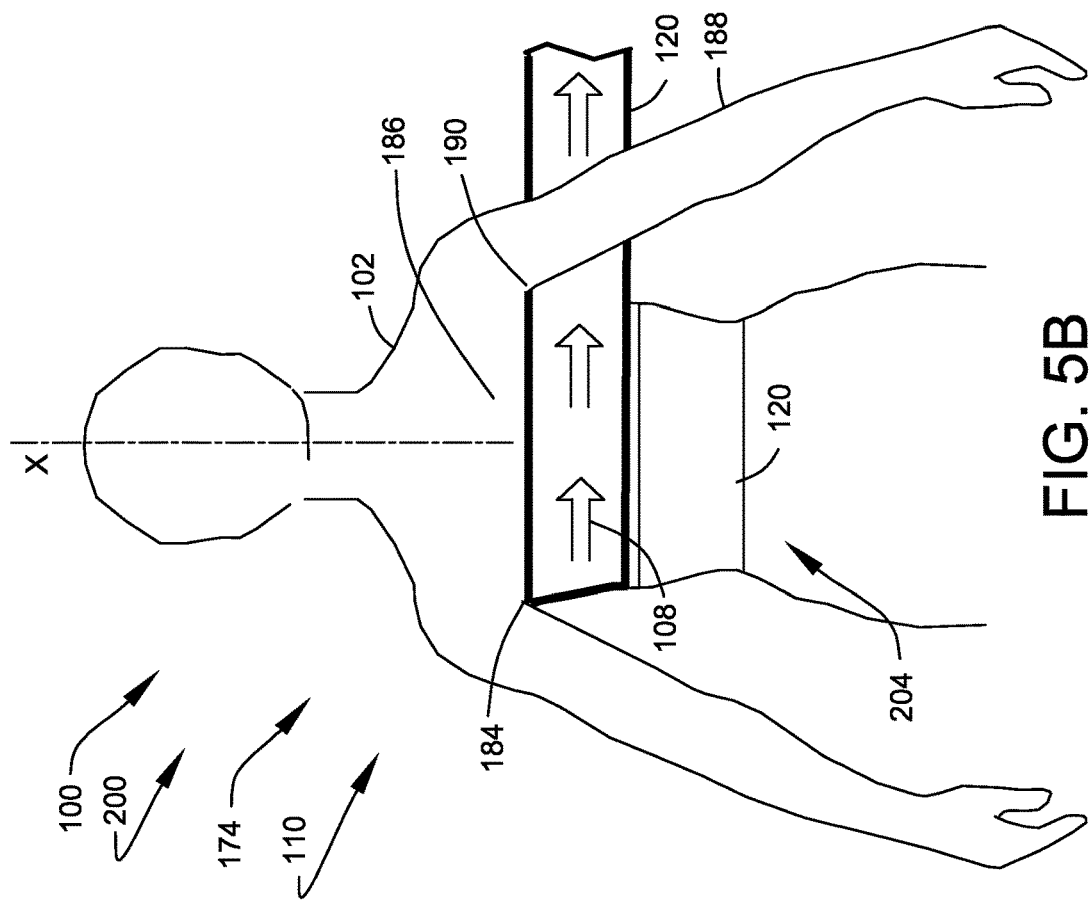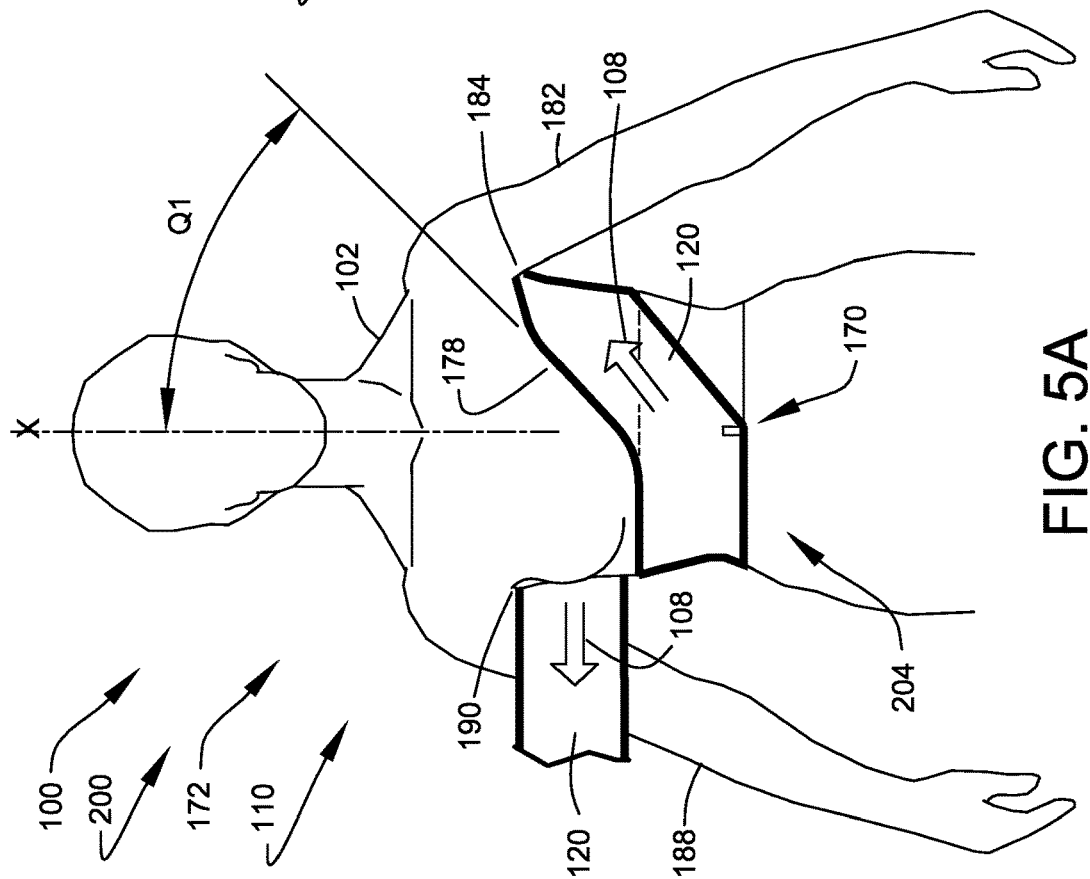

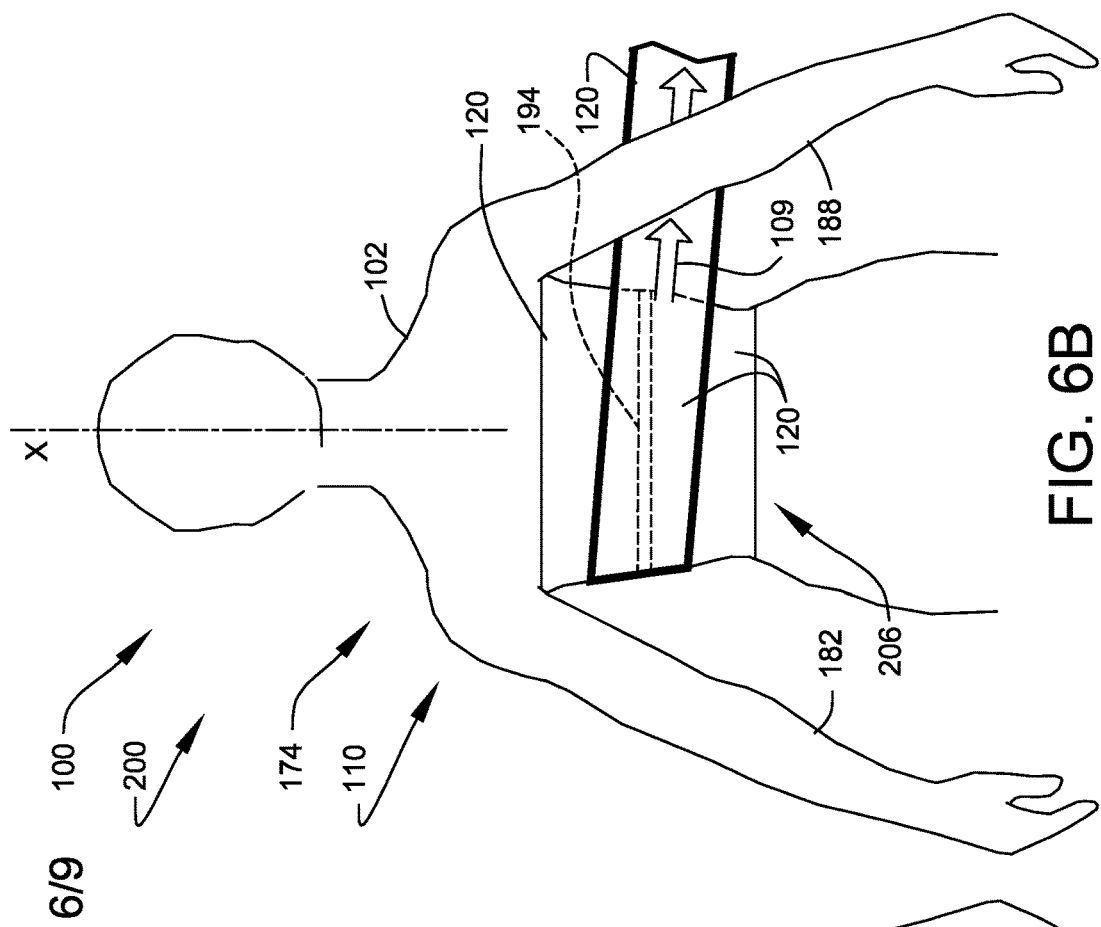
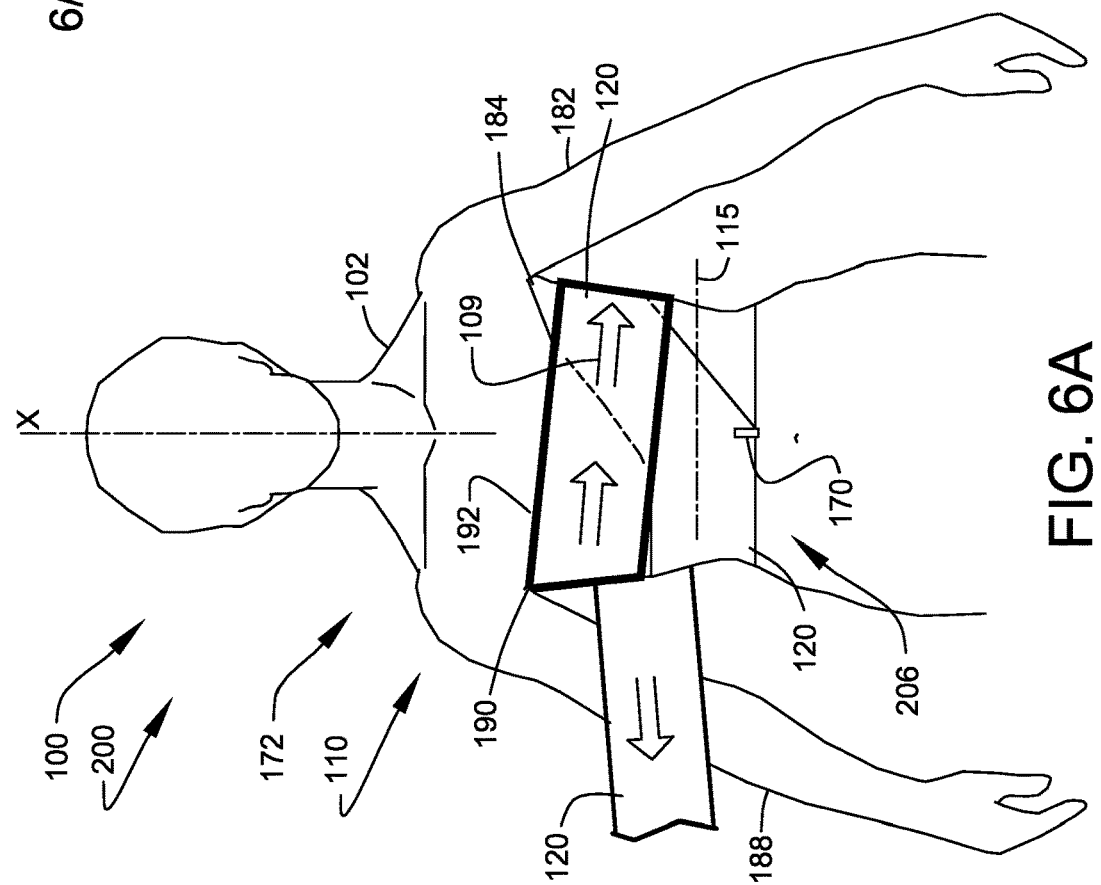

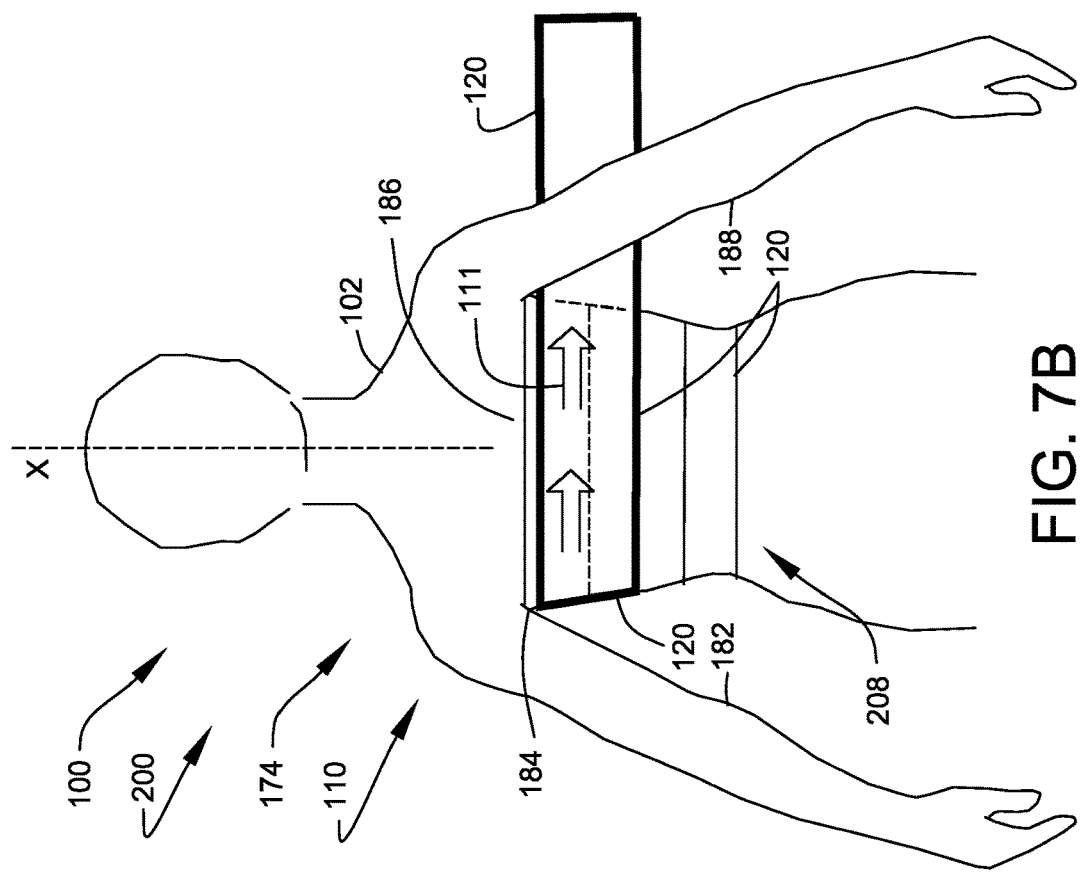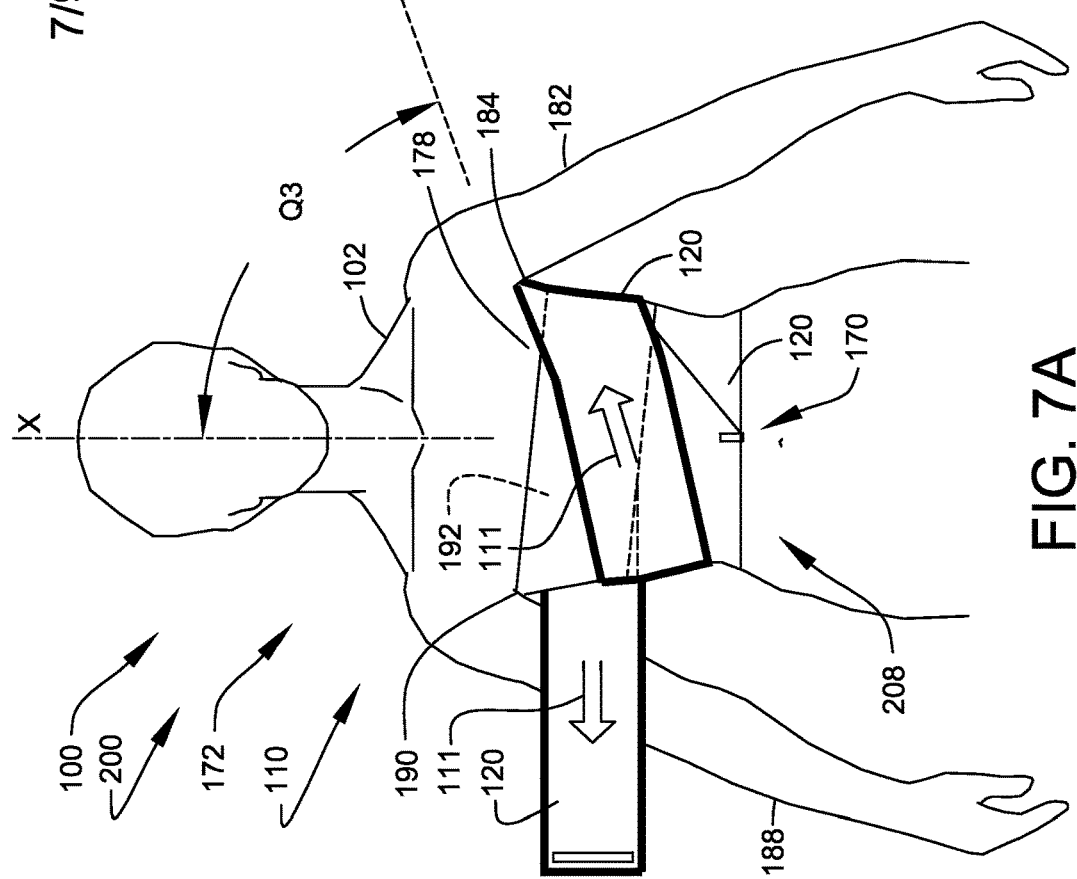

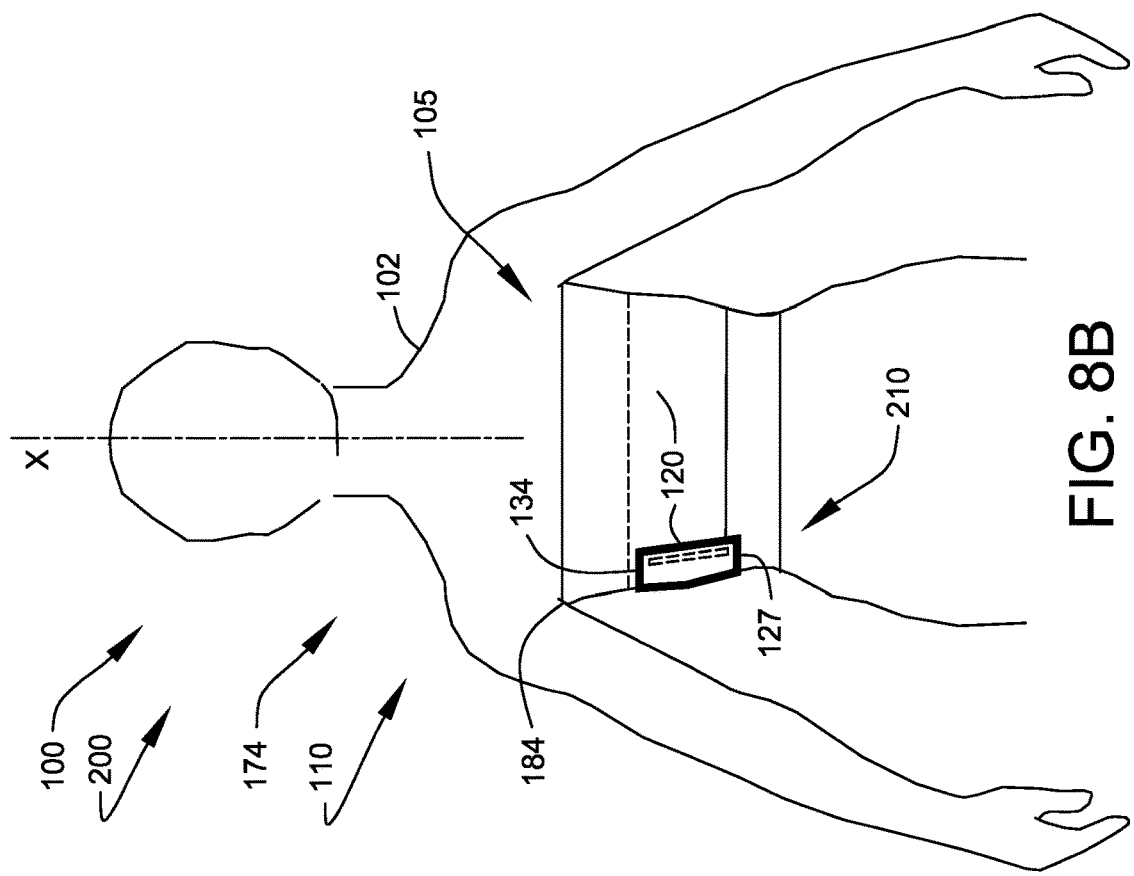
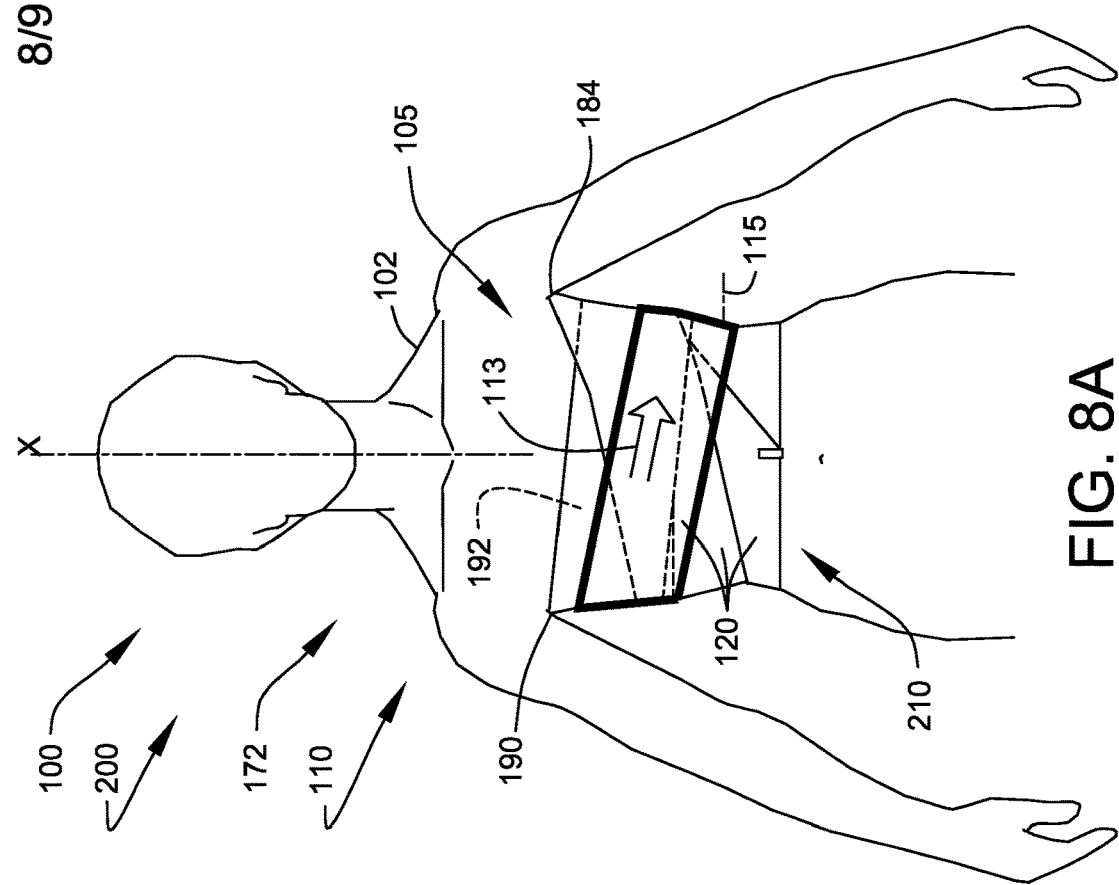

MEDICAL DRESSING SYSTEMS

CROSS-REFERENCE TO RELATED APPLICATION

The present application is related to and claims priority from prior provisional application Ser. No. 61/470,377, filed Mar. 31, 2011, entitled "MEDICAL DRESSING SYSTEMS"; and, this application is related to and claims priority from prior provisional application Ser. No. 61/505,056, filed Jul. 6, 2011, entitled "MEDICAL DRESSING SYSTEMS, the contents of all of which are incorporated herein by this reference and are not admitted to be prior art with respect to the present invention by the mention in this cross-reference section.

BACKGROUND

This invention relates to providing a system relating to improved medical dressing systems. More particularly, this invention relates to providing a system relating to an improvement in medical dressing techniques, improved medical dressing materials, and wound care.

There are many difficulties relating to medical dressings, including those used post-operatively, those used for battlefield wounds, those used for sports injuries, and more particularly, those used following breast cancer mastectomy. For example, medical dressings used post-operatively may not provide proper external force to maintain the integrity of incision lines such that suture material will not pull open as the patient moves. Furthermore, it is often difficult to determine wound conditions, such as, hemorrhaging and infection underneath medical dressings. Further, there are instances when medicines need to be applied to suture sites, and currently medical dressings must be removed prior to applying such medicine. Even further, surgical-drains and other medical-monitoring devices are often required for post-operative care, and improved methods for accommodating such medical-monitoring devices with medical dressings are needed.

OBJECTS AND FEATURES OF THE INVENTION

A primary object and feature of the present invention is to provide a system overcoming the above-mentioned problems.

It is a further object and feature of the present invention to provide such a system providing medical dressing for wrapping one or more wounds located on a body part of a patient. It is a further object and feature of the present invention to provide a medical dressing system which assists applying force to one or more wounds wrapped by the medical dressing. It is a further object and feature of the present invention to provide a medical dressing system which assists maintaining the integrity of one or more sutures wrapped by the medical dressing. Another object and feature of the present invention is to provide a medical dressing system which assists preventing the opening of one or more incision lines wrapped by the medical dressing. Another object and feature of the present invention is to provide a medical dressing system with elastomeric properties which minimally interfere with the mobility and breathability of a patient wrapped by the medical dressing.

It is another object and feature of the present invention is to provide a medical dressing system comprising wicking properties to assist removing exudates from one or more wounds wrapped by the medical dressing. Yet another object and feature of the present invention is to provide a medical dressing system comprising wicking properties to assist removing perspiration from one or more wound sites (and/or skin) wrapped by the medical dressing. Yet another object and feature of the present invention is to provide a medical dressing system with wicking properties to assist delivering one or more medicinal healing agents (such as for example, antibiotics) to a wound site wrapped by the medical dressing.

It is a further object and feature of the present invention to provide such a system for wrapping one or more wounds with a medical dressing to assist healing of such wounds. It is a further object and feature of the present invention to provide such a system for wrapping the torso of a patient with a medical dressing to assist healing of one or more post-mastectomy wounds. A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a system, relating to providing injury care for at least one wound located on at least one body part of at least one vertebrate life form, comprising: at least one wrapper structured and arranged to wrap the at least one wound and the at least one body part; and wherein such at least one wrapper comprises at least one exudate-transporter structured and arranged to transport at least one body exudate away from the at least one wound and at least one wound site surrounding the at least one wound; wherein such at least one wrapper further comprises at least one exudate-absorber structured and arranged to absorb such at least one body exudate transported away from the at least one wound and such at least one wound site by such at least one exudate-transporter; wherein such at least one wrapper further comprises torso-wrapability; wherein such at least one wrapper further comprises at least one uniter structured and arranged to unite such at least one exudate-transporter and such at least one exudate-absorber; wherein such at least one wrapper, when wrapped around the at least one wound and the at least one body part, provides injury care to the at least one wound.

Moreover, it provides such a system wherein such exudate-transporter comprises at least one first-exudate transporter and at least one second-exudate transporter each structured and arranged to transport such at least one body exudate away from the at least one wound and such at least one wound site surrounding the at least one wound. Additionally, it provides such a system further comprising at least one detectable-signal-generator structured and arranged to generate at least one detectable signal in response to such at least one body exudate. Also, it provides such a system further comprising: at least one exudate-identifier structured and arranged to identify such at least one body exudate as at least one body exudate species; wherein such at least one exudate-identifier comprises at least one distinct-signal-generator structured and arranged to generate at least one distinct such at least one detectable signal correlated with such at least one body exudate species. In addition, it provides such a system wherein such at least one detectable signal comprises at least one visual indication detectable by the naked-eye. And, it provides such a system wherein such at least one visual indication comprises at least one color change.

Further, it provides such a system wherein such at least one wrapper further comprises at least one stretch-potential-provider structured and arranged to provide stretch potential to such at least one wrapper. Even further, it provides such a system wherein such at least one stretch-potential-provider is further structured and arranged to permit at least resting-state breathability to the at least one vertebrate life form, when such at least one wrapper is wrapped around at least one torso region of the at least one vertebrate life form.

Moreover, it provides such a system further comprising at least one healing-agent-deliverer structured and arranged to deliver at least one healing agent from at least one outer surface of such at least one wrapper to the at least one wound. Additionally, it provides such a system wherein such at least one exudate-transporter comprises at least one flow-assistor structured and arranged to assist flow of such at least one body exudate away from the at least one wound and such at least one wound site.

Also, it provides such a system wherein such at least one flow-assistor comprises: at least one first unidirectional-flow-assistor structured and arranged to assist unidirectional flow of such at least one body exudate from the at least one wound to such at least one first exudate-transporter; at least one intermediate unidirectional-flow-assistor structured and arranged to assist unidirectional flow of such at least one body exudate from such at least one first exudate-transporter to such at least one exudate-absorber; at least one second unidirectional-flow-assistor structured and arranged to assist unidirectional flow of such at least one body exudate from such at least one exudate-absorber to such at least one second-exudate transporter; and at least one third unidirectional-flow-assistor structured and arranged to assist unidirectional flow of such at least one body exudate from such at least one second exudate-transporter to at least one outer surface of such at least one wrapper.

In addition, it provides such a system further comprising at least one adhesion-preventer structured and arranged to assist preventing at least one adhesion event between such at least one wrapper and the at least one wound. And, it provides such a system wherein such at least one adhesion-preventer further comprises at least one skin-adhesion preventer structured and arranged to assist preventing at least one adhesion event between such at least one wrapper and at least one skin portion of the at least one vertebrate life form wrapped by such at least one wrapper. Further, it provides such a system wherein such at least one exudate-transporter further comprises at least one perspiration-transporter structured and arranged to transport perspiration away from such at least one skin portion wrapped by such at least one wrapper.

Even further, it provides such a system further comprising at least one force-applier structured and arranged to apply force to the at least one body part wrapped by such at least one wrapper. Moreover, it provides such a system wherein such at least one force-applier comprises at least one suture-maintainer structured and arranged to assist maintaining the integrity of at least one suture wrapped by such at least one wrapper. Additionally, it provides such a system wherein such at least one force-applier comprises at least one incision-opening-preventer structured and arranged to assist preventing the opening of at least one incision line wrapped by such at least one wrapper.

Also, it provides such a system wherein such at least one wrapper further comprises at least one exudate-accumulation-indicator structured and arranged to indicate accumulation of such at least one body exudate on at least one outer surface of such at least one wrapper. In addition, it provides such a system wherein such at least one exudate-accumulation-indicator comprises at least one hemorrhage-indicator structured and arranged to indicate hemorrhaging of such at least one vertebrate life form. And, it provides such a system further comprising at least one fastener structured and arranged to fasten such at least one wrapper in at least one wrapped arrangement.

Further, it provides such a system wherein such at least one fastener comprises at least one first fastener structured and arranged to fasten such at least one wrapper in at least one intermediate wrapped arrangement. Even further, it provides such a system wherein such at least one fastener further comprises at least one second fastener structured and arranged to fasten such at least one wrapper in at least one final wrapped arrangement. Moreover, it provides such a system wherein such at least one fastener comprises at least one hook and loop fastener. Additionally, it provides such a system further comprising at least one container structured and arranged to contain at least one medical care item. Also, it provides such a system wherein such at least one medical care item comprises at least one surgical-drain. In addition, it provides such a system wherein such at least one container comprises at least one third fastener structured and arranged to fasten such at least one container to such at least one wrapper at at least one user-selected location.

And, it provides such a system further comprising at least one drain-tube-position-maintainer structured and arranged to maintain at least one drain tube of such at least one surgical drain in at least one user-selected position. Further, it provides such a system wherein such at least one third fastener comprises at least one hook and loop fastener.

In accordance with another preferred embodiment hereof, this invention provides a kit, relating to providing injury care for at least one wound located on at least one body part of at least one vertebrate life form, comprising: at least one medical dressing structured and arranged to wrap the at least one wound located on the at least one body part; at least one instruction set providing at least one set of instructions for using such at least one medical dressing; wherein such at least one medical dressing comprises at least one first exudate-transporter structured and arranged to transport at least one body exudate away from the at least one wound and at least one wound site surrounding the at least one wound, at least one exudate-absorber structured and arranged to absorb such at least one body exudate away from such at least one first exudate-transporter, at least one second exudate-transporter structured and arranged to transport such at least one exudate away from such at least one exudate-absorber, and torso-wrapability; wherein such at least one medical dressing, when wrapped around the at least one body part in at least one wrapped arrangement, provides injury care to the at least one wound.

Even further, it provides such a kit wherein such at least one instruction set describes a method, relating to wrapping the at least one wound in such at least one wrapped arrangement, comprising the steps of: placing at least one first terminal edge of the at least one medical dressing above at least one umbilicus area located on at least one abdominal region of the at least one vertebrate life form; aligning such at least one first terminal edge of the at least one medical dressing parallel to at least one vertical axis running parallel to at least one sagittal plane running vertically through the center of the at least one vertebrate life form; firmly wrapping the at least one medical dressing, radially with respect to such at least one vertical axis, horizontally across such at least one abdominal region and toward at least one dorsal side of the at least one torso region; continuing firmly wrapping the at least one medical dressing, radially with respect to such at least one vertical axis, horizontally across at least one lower back region and towards at least one ventral side of the at least one torso region; continuing firmly wrapping the at least one medical dressing, radially with respect to such at least one vertical axis, horizontally across such at least one abdominal region, completing at least one complete turn of the at least one medical dressing around at least one lower torso region of the at least one vertebrate life form; fastening the at least one medical dressing at at least one first fastening position, situate about above such at least one umbilicus area, with at least one first fastener; continuing firmly wrapping the at least one medical dressing, radially with respect to such at least one vertical axis, upward at an angle of from about forty degrees to about fifty degrees from such at least one first fastening position and across at least one breast portion of the at least one vertebrate life form; continuing firmly wrapping the at least one medical dressing, radially with respect to such at least on vertical axis, under at least one axilla of the at least one vertebrate life form, and toward such at least one dorsal side; continuing firmly wrapping the at least one medical dressing, radially with respect to such at least one vertical axis, horizontally across at least one upper back portion of the at least one vertebrate life form; continuing firmly wrapping the at least one medical dressing, radially with respect to such at least one vertical axis, under at least one opposing axilla of the at least one vertebrate life form and toward such at least one ventral side; continuing firmly wrapping the at least one medical dressing, radially with respect to such at least one vertical axis, downward at an angle of from about thirty degrees to about fifty degrees from such at least one opposing axilla, across at least one opposing breast portion of the at least one vertebrate life form, and towards such at least one dorsal side; continuing firmly wrapping the at least one medical dressing, radially with respect to such at least one vertical axis, horizontally across at least one middle back portion of the at least one vertebrate life form and toward such at least one ventral side; continuing firmly wrapping the at least one medical dressing, radially with respect to such at least one vertical axis, upward at an angle of from about forty degrees to about fifty degrees from under such at least one opposing breast portion and across such at least one breast portion; continuing firmly wrapping the at least one medical dressing, radially with respect to such at least one vertical axis, under such at least one axilla and toward such at least one dorsal side; continuing firmly wrapping the at least one medical dressing, radially with respect to such at least one vertical axis, horizontally across such at least one upper back portion; continuing firmly wrapping the at least one medical dressing, radially with respect to such at least one vertical axis, under such at least one opposing axilla and towards such at least one ventral side; continuing firmly wrapping the at least one medical dressing, radially with respect to such at least one vertical axis, downward at an angle of from about thirty degrees to about fifty degrees from such at least one opposing axilla, across such at least opposing breast portion, and towards such at least one dorsal side; and fastening at least one second terminal edge of the at least one medical dressing, with at least one second fastener, at at least one second fastening position located on the at least one wrapped arrangement situate about such at least one lower torso region; wherein the at least one wrapped arrangement, formed by the method, provides mechanical force to compress the at least one wound covered by the at least one wrapped arrangement to assist healing of the at least one wound, while maintaining the mobility and breathability of the at least one vertebrate life form.

Moreover, it provides such a kit further comprising: at least one container structured and arranged to contain at least one surgical-drain; wherein such at least one container comprises at least one fastener structured and arranged to fasten such at least one container to such at least one medical dressing. Additionally, it provides such a kit wherein such at least one instruction set comprises at least one instruction booklet. Also, it provides such a kit wherein such at least one instruction set comprises at least one compact-disc. In addition, it provides such a kit wherein such at least one instruction set is readable over the internet.

In accordance with another preferred embodiment hereof, this invention provides a method, relating to wrapping at least one wound, located on at least one torso region of at least one vertebrate life form, with at least one medical dressing in at least one wrapped arrangement, comprising the steps of: placing at least one first terminal edge of the at least one medical dressing above at least one umbilicus area located on at least one abdominal region of the at least one vertebrate life form; aligning such at least one first terminal edge of the at least one medical dressing parallel to at least one vertical axis running parallel to at least one sagittal plane running vertically through the center of the at least one vertebrate life form; firmly wrapping the at least one medical dressing, radially with respect to such at least one vertical axis, horizontally across such at least one abdominal region and toward at least one dorsal side of the at least one torso region; continuing firmly wrapping the at least one medical dressing, radially with respect to such at least one vertical axis, horizontally across at least one lower back region and towards at least one ventral side of the at least one torso region; continuing firmly wrapping the at least one medical dressing, radially with respect to such at least one vertical axis, horizontally across such at least one abdominal region, completing at least one complete turn of the at least one medical dressing around at least one lower torso region of the at least one vertebrate life form; fastening the at least one medical dressing at at least one first fastening position, situate about above such at least one umbilicus area, with at least one first fastener; continuing firmly wrapping the at least one medical dressing, radially with respect to such at least one vertical axis, upward at an angle of from about forty degrees to about fifty degrees from such at least one first fastening position and across at least one breast portion of the at least one vertebrate life form; continuing firmly wrapping the at least one medical dressing, radially with respect to such at least on vertical axis, under at least one axilla of the at least one vertebrate life form, and toward such at least one dorsal side; continuing firmly wrapping the at least one medical dressing, radially with respect to such at least one vertical axis, horizontally across at least one upper back portion of the at least one vertebrate life form; continuing firmly wrapping the at least one medical dressing, radially with respect to such at least one vertical axis, under at least one opposing axilla of the at least one vertebrate life form and toward such at least one ventral side; continuing firmly wrapping the at least one medical dressing, radially with respect to such at least one vertical axis, downward at an angle of from about thirty degrees to about fifty degrees from such at least one opposing axilla, across at least one opposing breast portion of the at least one vertebrate life form, and towards such at least one dorsal side; continuing firmly wrapping the at least one medical dressing, radially with respect to such at least one vertical axis, horizontally across at least one middle back portion of the at least one vertebrate life form and toward such at least one ventral side; continuing firmly wrapping the at least one medical dressing, radially with respect to such at least one vertical axis, upward at an angle of from about forty degrees to about fifty degrees from under such at least one opposing breast portion and across such at least one breast portion; continuing firmly wrapping the at least one medical dressing, radially with respect to such at least one vertical axis, under such at least one axilla and toward such at least one dorsal side; continuing firmly wrapping the at least one medical dressing, radially with respect to such at least one vertical axis, horizontally across such at least one upper back portion; continuing firmly wrapping the at least one medical dressing, radially with respect to such at least one vertical axis, under such at least one opposing axilla and towards such at least one ventral side; continuing firmly wrapping the at least one medical dressing, radially with respect to such at least one vertical axis, downward at an angle of from about thirty degrees to about fifty degrees from such at least one opposing axilla, across such at least opposing breast portion, and towards such at least one dorsal side; and fastening at least one second terminal edge of the at least one medical dressing, with at least one second fastener, at at least one second fastening position located on the at least one wrapped arrangement situate about such at least one lower torso region; wherein the at least one wrapped arrangement, formed by the method, provides mechanical force to compress the at least one wound covered by the at least one wrapped arrangement to assist healing of the at least one wound, while maintaining the mobility and breathability of the at least one vertebrate life form.

In accordance with another preferred embodiment hereof, this invention provides a method, relating to wrapping at least one wound located on at least one body part, divided into at least one first body section and at least one second body section by at least one coronal plane running vertically through the center of the at least one body part, of at least one vertebrate life form with at least one medical dressing to form at least one wrapped arrangement, comprising the steps of: aligning at least one first terminal edge of the at least one medical dressing parallel to at least one vertical axis running vertically through the center of the at least one body part; firmly wrapping the at least one medical dressing, radially with respect to such at least one vertical axis, horizontally across at least one the first body section; continuing firmly wrapping the at least one medical dressing, radially with respect to such at least one vertical axis, horizontally across the at least one second body section; continuing firmly wrapping the at least one medical dressing, radially with respect to such at least one vertical axis, horizontally across such at least one first body section, creating at least one complete turn around the at least one body part; fastening the at least one medical dressing, with at least one first fastener, at at least one first fastening position situate about such at least one first terminal edge; continuing firmly wrapping the at least one medical dressing, radially with respect to such at least one vertical axis, upward at an angle of from about forty degrees to about fifty degrees from such at least one first fastening position across the at least one first body section; continuing firmly wrapping the at least one medical dressing, radially with respect to such at least one vertical axis, horizontally across the at least one second body section; continuing firmly wrapping the at least one medical dressing, radially with respect to such at least one vertical axis, downward at an angle of from about thirty degrees to about fifty degrees across the at least one first body section; continuing firmly wrapping the at least one medical dressing, radially with respect to such at least one vertical axis, horizontally across the at least one second body section; continuing firmly wrapping the at least one medical dressing, radially with respect to such at least one vertical axis, upward at an angle of from about forty degrees to about fifty degrees across the at least one first body section; continuing firmly wrapping the at least on medical dressing, radially with respect to such at least one vertical axis, horizontally across the at least one second body section; continuing firmly wrapping the at least one medical dressing, radially with respect to such at least one vertical axis, downward at an angle of from about thirty degrees to about fifty degrees across the at least one first body section; and fastening at least one second terminal edge of the at least one medical dressing with at least one second fastener on the at least one wrapped arrangement; wherein the at least one wrapped arrangement, formed by the method, provides mechanical force to compress at least one wound covered by the at least one medical dressing to assist healing of the at least one wound, while maintaining the mobility and breathability of the at least one vertebrate life form.

In accordance with another preferred embodiment hereof, this invention provides a system, relating to providing injury care for at least one wound located on at least one body part of at least one vertebrate life form, comprising: wrapper means for wrapping the at least one wound and the at least one body part; wherein such wrapper means comprises exudate-transporter means for transporting at least one body exudate away from the at least one wound and at least one wound site surrounding the at least one wound; wherein such wrapper means comprises exudate-absorber means for absorbing such at least one body exudate transported away from the at least one wound and such at least one wound site by such exudate-transporter means; wherein such wrapper means further comprises torso-wrapability; wherein such wrapper means comprises uniter means for uniting such exudate-transporter means and such exudate-absorber means; and, wherein such wrapper means, when wrapped around the at least one body part, assists providing injury care to the at least one wound. And, it provides such a system wherein such exudate-transporter means comprises first-exudate transporter means. Further, it provides such a system further comprising detectable-signal-generator means for generating at least one detectable signal in response to such at least one body exudate. Even further, it provides such a system further comprising: exudate-identifier means for identifying such at least one body exudate as at least one body exudate species; wherein such at least one exudate-identifier comprises at least one distinct-signal-generator structured and arranged to generate at least one distinct such at least one detectable signal correlated with such at least one body exudate species.

Even further, it provides such a system further comprising stretch-potential-provider means for providing stretch potential to such at least one wrapper means. Even further, it provides such a system further comprising healing-agent-deliverer means for delivering at least one healing agent from at least one outer surface of such wrapper means to the at least one wound. Even further, it provides such a system wherein such exudate-transporter means comprises flow-assistor means for assisting flow of such at least one body exudate away from the at least one wound and such at least one wound site. Even further, it provides such a system wherein such flow-assistor means comprises: first unidirectional-flow-assistor means for assisting unidirectional flow of such at least one body exudate from the at least one wound to such first exudate-transporter means; intermediate unidirectional-flow-assistor means for assisting unidirectional flow of such at least one body exudate from such first exudate-transporter means to such exudate-absorber means; second unidirectional-flow-assistor means for assisting unidirectional flow of such at least one body exudate from such exudate-absorber means to such second exudate-transporter means; and third unidirectional-flow-assistor means for assisting flow of such at least one body exudate from such second exudate-transporter to at least one outer surface of such wrapper means. Even further, it provides such a system further comprising adhesion-preventer means for assisting preventing at least one adhesion event between such wrapper means and the at least one wound. Even further, it provides such a system wherein such adhesion-preventer means comprises skin-adhesion preventer means for assisting preventing at least one adhesion event between such wrapper means and at least one skin portion of the at least one vertebrate life form wrapped by such wrapper means.

Even further, it provides such a system wherein such exudate-transporter means further comprises perspiration-transporter means for transporting perspiration away from such at least one skin portion wrapped by such wrapper means. Even further, it provides such a system further comprising force-applier means for applying force to the at least one body part wrapped by such wrapper means. Even further, it provides such a system wherein such force-applier means comprises suture-maintainer means for assisting maintaining the integrity of at least one suture wrapped by such wrapper means. Even further, it provides such a system wherein such force-applier means comprises incision-opening-preventer means for assisting preventing opening of at least one incision line wrapped by such wrapper means.

Even further, it provides such a system further comprising exudate-accumulation-indicator means for indicating accumulation of at least one body exudate on at least one outer surface of such wrapper means. Even further, it provides such a system wherein such exudate-accumulation-indicator means comprises hemorrhage-indicator means for indicating hemorrhaging of such at least one vertebrate life form. Even further, it provides such a system further comprising fastener means for fastening such wrapper means in at least one wrapped arrangement. Even further, it provides such a system wherein such fastener means comprises first fastener means for fastening such wrapper means in at least one intermediate wrapped arrangement. Even further, it provides such a system wherein such fastener means further comprises second fastener means for fastening such wrapper means in at least one final wrapped arrangement. Even further, it provides such a system further comprising container means for containing at least one surgical drain. Even further, it provides such a system wherein such container means comprises third fastener means for fastening such container means to such wrapper means. Even further, it provides such a system further comprising drain-tube-position-maintainer means for maintaining at least one drain tube of such at least one surgical drain in at least one user-selected position.

In accordance with another preferred embodiment hereof, this invention provides a system, relating to providing injury care for at least one wound located on at least one body part of at least one vertebrate life form, comprising: wrapper means for wrapping the at least one wound and the at least one body part; and transporter means for transporting at least one body exudate away from the at least one wound and at least one wound site surrounding the at least one wound; wherein such transporter means comprises first transporter means and second transporter means for transporting at least one body exudate away from the at least one wound and at least one wound site surrounding the at least one wound; first geometry means for providing such wrapper means with such transporter means; absorber means for absorbing such at least one body exudate transported away from the at least one wound and such at least one wound site by such transporter means; second geometry means for providing such wrapper means with such absorber means; wherein such wrapper means comprises third geometry means for providing such wrapper means with torso-wrapability; and uniter means for uniting such transporter means, such first geometry means, such absorber means, such second geometry means, and such third geometry means wherein such wrapper means, when wrapped around the at least one body part, assists providing injury care to the at least one wound.

In addition, this invention provides every novel feature, element, combination, step and/or method suggested by this patent application.

BRIEF DESCRIPTION OF THE DRAWINGS

FIG. 2A shows a front view, illustrating a bandage of the medical dressing systems, according the preferred embodiment of FIG. 1.

FIG. 2B shows a sectional view, through the section 2B-2B of FIG. 2A, illustrating multiple layers of the bandage, according to the preferred embodiment of FIG. 1.

FIG. 2C shows a sectional view, through the section 2C-2C of FIG. 2A, illustrating dispersion of a chemical alert substance throughout the bandage, according to an alternately preferred embodiment of the present invention.

FIG. 3A shows a front view, illustrating a pocket of the medical dressing, according the preferred embodiment of FIG. 1.

FIG. 3B shows a rear view, illustrating the pocket of the medical dressing, according to the preferred embodiment of FIG. 1.

FIG. 3C shows a sectional view, through the section 3C-3C of FIG. 3A, illustrating attachment of the pocket to the bandage using securing strips, according the preferred embodiment of FIG. 1.

FIG. 4A shows a front view, illustrating a first wrapping step of a wrapping technique of medical dressing systems, according the preferred embodiment of FIG. 1.

FIG. 4B shows a rear view, illustrating the first wrapping step of the wrapping technique of medical dressing systems, according the preferred embodiment of FIG. 1.

FIG. 5A shows a front view, illustrating a second wrapping step of the wrapping technique, according the preferred embodiment of FIG. 1.

FIG. 5B shows a rear view, illustrating the second wrapping step of the wrapping technique, according the preferred embodiment of FIG. 1.

FIG. 6A shows a front view, illustrating a third wrapping step of the wrapping technique, according the preferred embodiment of FIG. 1.

FIG. 6B shows a rear view, illustrating the third wrapping step of the wrapping technique, according the preferred embodiment of FIG. 1.

FIG. 7A shows a front view, illustrating a fourth wrapping step of the wrapping technique, according the preferred embodiment of FIG. 1.

FIG. 7B shows a rear view, illustrating the fourth wrapping step of the wrapping technique, according the preferred embodiment of FIG. 1.

FIG. 8A shows a front view, illustrating a fifth wrapping step of the wrapping technique, according the preferred embodiment of FIG. 1.

FIG. 8B shows a rear view, illustrating a fifth wrapping step of the wrapping technique, according to the preferred embodiment of FIG. 1.

DETAILED DESCRIPTION OF THE BEST MODES AND PREFERRED EMBODIMENTS OF THE INVENTION

Figure 1:
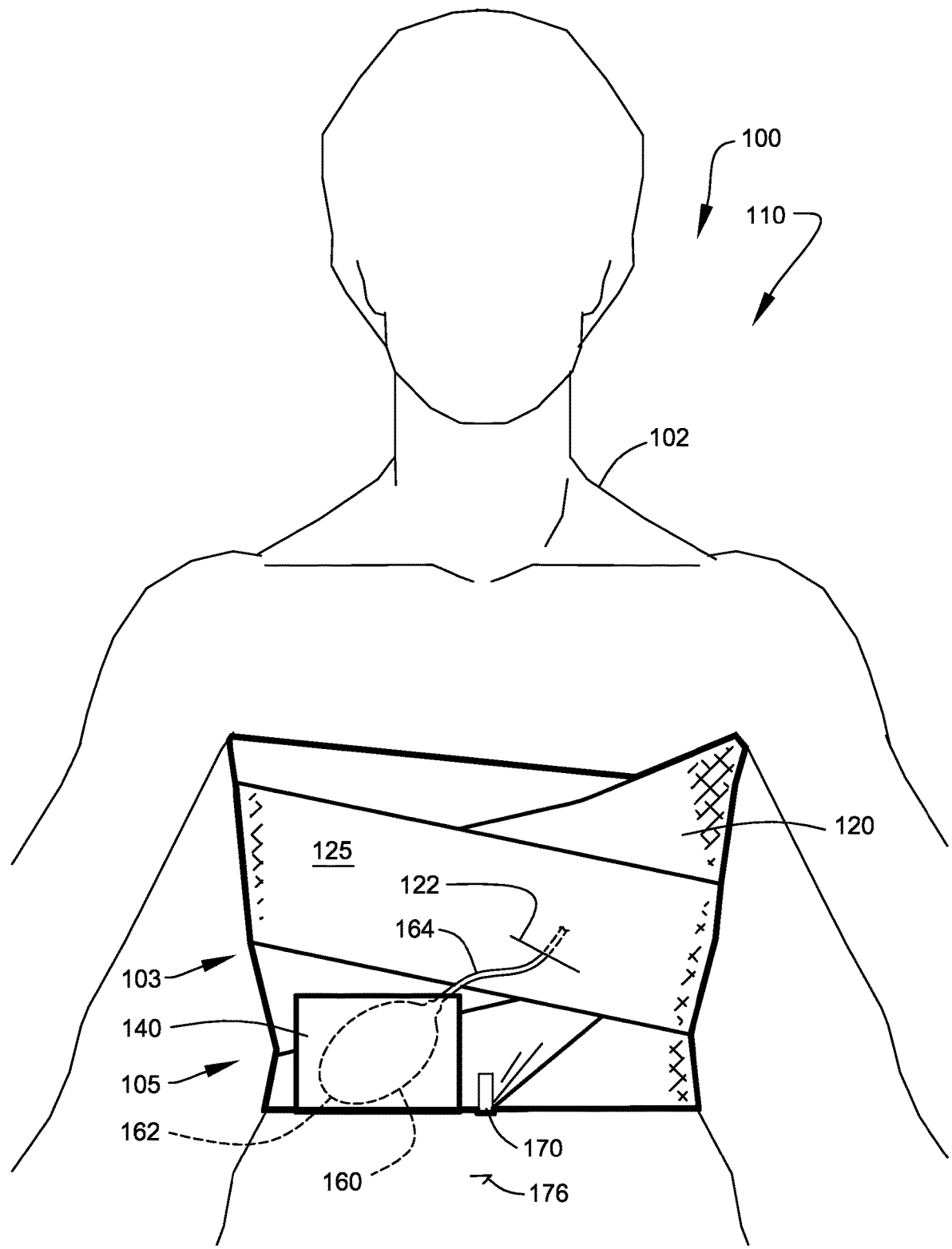
FIG. 1 shows a front view, illustrating a medical dressing of the medical dressing systems, according to a preferred embodiment of the present invention.

FIG. 1 shows a perspective view, illustrating medical dressing 103 of medical dressing systems 100, according to a preferred embodiment of the present invention. Medical dressing 103 preferably provides wound management to at least one patient 102 (see further details below). In use, medical dressing 103 (at least embodying herein at least one wrapper structured and arranged to wrap the at least one wound and the at least one body part; and at least embodying herein wrapper means for wrapping the at least one wound and the at least one body part) preferably is wrapped around at least one body part of patient 102 comprising at least one wound (hereinafter such at least one wound is referred to as "a wound"), preferably covering such at least one body part of patient 102, as shown. Patient 102 preferably comprises a human in need of wound management for a wound, as shown. Alternately preferably, patient 102 preferably comprises at least one vertebrate life form in need of wound management for a wound (such as, for example, dogs, cats, horses and other such animals). A wound, as described herein, preferably comprises: at least one post-operative mastectomy wound; alternately preferably, at least one post-operative cosmetic surgery wound; alternately preferably, at least one post-operative suture; alternately preferably, at least one post-operative incision; alternately preferably, at least one sports injury, alternately preferably, at least one bone injury, alternately preferably, at least one muscle injury; alternately preferably at least one soft-tissue injury; alternately preferably, at least one internal injury; alternately preferably, at least one injury occurring during combat situations. Upon reading this specification, those with ordinary skill in the art will now appreciate that, under appropriate circumstances, considering such issues as design preference, user preference, user needs, etc., other types of wounds, such as, for example, burns, inflammations, post-lumpectomy wounds, any type of wound resulting in broken skin, bruises, etc., may suffice.

A wound, as described herein, preferably is localized to at least one wound site (hereinafter such at least one wound site is referred to as "a wound site"). A wound site, as described herein, preferably comprises a wound and the affected adjacent surrounding tissues (skin and fur, as applicable) surrounding a wound.

Medical dressing 103 preferably is structured and arranged to wrap such at least one body part comprising a wound (hereinafter such at least one body part is referred to as "a body part"). A body part, as described herein, preferably comprises at least one region of torso 110, as shown. Alternately preferably, a body part preferably comprises at least one appendage of patient 102, alternately preferably at least one neck portion of patient 102, alternately preferably at least one hand of patient 102, alternately preferably at least one foot of patient 102, alternately preferably at least one shoulder of patient 102, alternately preferably the head of patient 102. Upon reading this specification, those with ordinary skill in the art will now appreciate that, under appropriate circumstances, considering such issues as design preference, user preference, user needs, etc., other body parts, such as, for example, knees, elbows, waist, fingers, multiple body parts, etc., may suffice.

Wound management, as described herein, preferably comprises providing sufficient mechanical force, through compression to a wound site, to promote healing of a wound of patient 102, while preferably maintaining the comfort, mobility, and breathability of patient 102. Wound management, as described herein, further comprises assisting promoting wound stability, assisting maintaining wound integrity, assisting promoting suture integrity, assisting soft tissue stability, assisting hemodynamic stability (blood flow), assisting edema reduction, and assisting maintaining proper blood circulation. In addition, wound management, as described herein, preferably further comprises assisting maintaining the integrity of sutures and incision lines, even while patient 102 breathes and moves.

Wound management, as described herein, further comprises assisting transporting wound exudates away from a wound site (see further details below). Wound exudates, as described herein, preferably comprise blood, alternately preferably infectious drainage, alternately preferably lymph, alternately preferably serous fluids, alternately preferably other drainage, alternately preferably other biological fluids or waste products capable of being released from such at least one wound site, alternately preferably at least one mixture of any of the above described wound exudate compositions.

Furthermore, wound management, as described herein, preferably comprises assisting transporting perspiration away from a body part covered by medical dressing 103, including perspiration from a wound site as well as perspiration from the skin covered by medical dressing 103. Such assisting transporting wound exudates and perspiration away from a wound site and/or the skin covered by medical dressing 103 preferably occurs by at least one wicking action of medical dressing 103 (see further details below). Such assisting transporting wound exudates and perspiration away from a wound site and/or the skin covered by medical dressing 103 preferably at least assists to minimize the level of bacteria on the skin surface covered by medical dressing 103. In addition, such assisting transporting perspiration away from a wound sit and/or the skin covered by medical dressing 103 preferably assists maintaining the body warmth of patient 102. In addition, such assisting transporting wound exudates and perspiration away from a wound site and/or the skin covered by medical dressing 103 preferably further assists keeping patient 102 comfortable and dry.

Wound management, when applied to sports-related injuries, further comprises assisting athletic participation of patient 102 and minimizing "down time". More particularly, medical dressing 103 preferably assists patient 102 to return to athletic participation by stabilizing a wound with a non-cumbersome wrap which minimally interferes with the mobility of patient 102.

Wound management, as described herein, further comprises allowing early detection of certain problems associated with the healing process, such as infections, hemorrhaging conditions, or other complications resulting from injuries or surgical procedures (see further details below).

Wound management, as described herein, further comprises assisting delivering of at least one healing agent (hereinafter referred to as "a healing agent") to a wound covered by medical dressing 103. Such assisting delivering of a medicine or a healing agent preferably does not require the removal of medical dressing 103, and preferably occurs by the wicking action of medical dressing 103 (see further details below).

Medical dressing 103 preferably comprises at least one bandage 120, as shown. Bandage 120 preferably is structured and arranged to wrap at least one wound, as shown. Medical dressing 103 preferably optionally comprises at least one pocket 140, as shown. Pocket 140 preferably is structured and arranged to contain at least one surgical drain assembly 160, as shown (this arrangement at least embodying herein at least one container structured and arranged to contain at least one medical care item). Alternately preferably, pocket 140 preferably is structured and arranged to contain a medicine, alternately preferably a healing agent, alternately preferably at least one other medical care item. Upon reading this specification, those with ordinary skill in the art will now appreciate that, under appropriate circumstances, considering such issues as design preference, user preference, user needs, available materials, technological advances, etc., other medical care items, such as, for example, bandages, medical supplies, etc., may suffice. Upon reading this specification, those with ordinary skill in the art will now appreciate that, under appropriate circumstances, considering such issues as design preference, user preference, user needs, available materials, technological advances, etc., other pocket arrangements, such as, for example, multiple pockets for multiple surgical drains, multiple pockets for various medical care items, etc., may suffice.

Bandage 120 preferably is wrapped around a body part requiring wound management, as shown. Bandage 120 preferably is easily removed during changing, adjusting, or treating patient 102 and preferably does not stick to a wound site or the skin of patient 102 causing discomfort to patient 102 (this arrangement at least embodying herein at least one adhesion-preventer structured and arranged to assist preventing at least one adhesion event between such at least one wrapper and the at least one wound; and this arrangement at least herein embodying wherein such at least one adhesion-preventer further comprises at least one skin-adhesion preventer structured and arranged to assist preventing at least one adhesion event between such at least one wrapper and at least one skin portion of the at least one vertebrate life form wrapped by such at least one wrapper). The composition of bandage 120 is described in greater detail below.

Pocket 140 preferably is manufactured separately from bandage 120. Pocket 140 preferably is attached to bandage 120 by at least one securing member 152 (see FIG. 3B and further details below). Pocket 140 preferably may be removably attached (detachable) from bandage 120. Pocket 140 preferably may be attached to bandage 120 at any user-selected position. The attachment site for pocket 140 preferably is selectable to assist medical treatment of patient 102 according to treatment strategies and the wound management needs of patient 102.

Pocket 140 preferably is structured and arrangement to support at least one surgical drain assembly 160, as shown. Surgical drain assembly 160 preferably is structured and arranged to collect pus, blood, other wound exudates, or other biological fluids released from a wound. Surgical drain assembly 160 preferably comprises at least one drain 162 and at least one drain tubing 164, as shown. Drain tubing 164 preferably inserts into or adjacent a wound in order to preferably capture pus, blood, other wound exudates, or other biological fluids being released from a wound. Such biological fluids preferably pass from a wound through drain tubing 164 for subsequent collection in drain 162. Surgical drain assembly 160 preferably comprises a plurality of available medical surgical drain assemblies comprising tubing. Upon reading this specification, those with ordinary skill in the art will now appreciate that, under appropriate circumstances, considering such issues as design preference, user preferences, marketing preferences, cost, structural requirements, available materials, technological advances, etc., other drainage arrangements such as, for example, direct drainage with no tubing, suction devices, absorptive collecting devices, etc., may suffice.

Bandage 120 preferably comprises at least one portal 122, as shown. Portal 122 (at least embodying herein at least one drain-tube-position-maintainer structured and arranged to maintain at least one drain tube of such at least one surgical drain in at least one user-selected position) preferably is employed to assist maintaining drain tubing 164 in position, as shown. In addition, portal 122 preferably is employed to assist preventing drain tubing 164 from dislodging from a wound. In addition, portal 122 preferably is employed to assist preventing drain tubing 164 from shifting within a wound and disturbing a wound. Drain tubing 164 preferably is inserted through portal 122 of bandage 120, as shown. Portal 122 preferably comprises at least one aperture in bandage 120, alternately preferably at least one eyelet in bandage 120, alternately preferably at least one slit in bandage 120, as shown. Portal 122 preferably is created by patient 102, or at least one caretaker of patient 102, by cutting bandage 120 at at least one preferred position. Alternately preferably, bandage 120 preferably is manufactured with at least one portal 122. Upon reading this specification, those with ordinary skill in the art will now appreciate that, under appropriate circumstances, considering such issues as design preference, user preference, user needs, structural requirements, available materials, technological advances, etc., other arrangements for maintaining surgical drain assembly 160 in position, such as, for example, clips, clasps, adhesive tape, hook and loop fasteners, other fastening arrangements, etc., may suffice.

Medical dressing 103 preferably may be optionally employed to deliver a healing agent to a wound site wrapped by medical dressing 103. More particularly, a healing agent preferably may be applied to at least one outer surface 125 of medical dressing 103 covering a wound site, preferably allowing a healing agent to be delivered to a wound site by the wicking action of medical dressing 103 (this arrangement at least embodying herein at least one healing-agent-deliverer structured and arranged to deliver at least one healing agent from at least one outer surface of such at least one wrapper to the at least one wound). A healing agent preferably comprises at least one water-soluble antibacterial/antimicrobial treatment, alternatively preferably at least one water-soluble medication. The above described arrangement preferably allows patient 102, or at least one caretaker of patient 102, to apply a healing agent to a wound site without having to un-wrap medical dressing 103 once applied to patient 102, as shown. Upon reading this specification, those with ordinary skill in the art will now appreciate that, under appropriate circumstances, considering such issues as design preference, user preference, user needs, structural requirements, available materials, technological advances, wound site, wound type, etc., other healing agent application arrangements, such as, for example, bandage-embedded medications placed directly against a wound, etc., may suffice.

Medical dressing 103 preferably is manufactured and available to consumers in a variety of colors, such as, for example, flesh-tone for standard use, pink for breast cancer patients (post-mastectomy patients), purple for Crohn's patients, red for heart-related wound management, as well as other colors associated with other diseases or injuries. Colors for medical dressing 103 preferably are used to assist empowerment of medical dressing 103 users in a more positive manner throughout all phases of healing and, to preferably assist users to feel more capable in the ability to take care of their own needs. Upon reading this specification, those with ordinary skill in the art will now appreciate that, under appropriate circumstances, considering such issues as design preference, user preference, manufacturer preference, structural requirements, available materials, etc., other medical dressing design arrangements, such as, for example, other colors, designs, patterns, prints, etc., may suffice.

In addition, medical dressing 103 preferably is manufactured and made available in a variety of sport colors to simulate team or individual uniform colors as well as bold colors, if employed for wound management of sports-related injuries. Such sport colors preferably comprise bright colors to preferably assist empowering athletes to perform despite an injury. Upon reading this specification, those with ordinary skill in the art will now appreciate that, under appropriate circumstances, considering such issues as design preference, user preference, manufacturer preference, structural requirements, available materials, etc., other medical dressing design arrangements, such as, for example, other colors, designs, patterns, prints, etc., may suffice.

Medical dressing 103 preferably is at least employed for wound management, preferably torso wound management, preferably chest wound management, preferably post-operative mastectomy wound management. Mastectomy, as described herein, preferably comprises any type of mastectomy of one or both breasts, preferably comprising any type of full or partial mastectomy, radical or modified radical mastectomy, or skin-sparing or nipple-sparing mastectomy.

When employed for post-operative mastectomy wound management, bandage 120 of medical dressing 103 preferably is wrapped around torso 110 in at least one chest-wrap arrangement 105, as shown in FIG. 1. At least one wrapping technique 200 preferably is employed to wrap bandage 120 around torso 110 of patient 102 preferably forming chest-wrap arrangement 105 (see FIG. 4A through FIG. 8B and further details below) (this arrangement at least herein embodying wherein such at least one wrapper further comprises torso-wrapability; and this arrangement at least herein embodying wherein such wrapper means further comprises torso-wrapability). According to wrapping technique 200, bandage 120 preferably is wrapped around torso 110 multiple times in a circular fashion, preferably from ventral side 172 of torso 110 (see FIG. 4A) to dorsal side 174 of torso 110 (see FIG. 4B) and finally secured (see FIG. 4A through FIG. 8B and further details below). Upon reading this specification, those with ordinary skill in the art will now appreciate that, under appropriate circumstances, considering such issues as design preference, user preferences, marketing preferences, cost, structural requirements, available materials, technological advances, etc., other wrap arrangements such as, for example, dorsal to ventral, etc., may suffice.

In chest-wrap arrangement 105, medical dressing 103 preferably assists post-operative breast augmentation. Furthermore, in chest-wrap arrangement 105, medical dressing 103 preferably assists post-operative wound reduction resulting from mastectomy procedures. In chest-wrap arrangement 105, medical dressing 103 preferably supplies sufficient mechanical force to compress a wound site to preferably assist promoting healing of a wound (this arrangement at least embodying herein at least one force-applier structured and arranged to apply force to the at least one body part wrapped by such at least one wrapper). More particularly, medical dressing 103, when wrapped in chest-wrap arrangement 105, preferably supplies sufficient external force around torso 110 to assist maintaining the integrity of and to assist preventing the opening of surgical incision lines, sutures, and stitches resulting from post-mastectomy procedures (this arrangement at least herein embodying wherein such at least one force-applier comprises at least one suture-maintainer structured and arranged to assist maintaining the integrity of at least one suture wrapped by such at least one wrapper; and this arrangement at least herein embodying wherein such at least one force-applier comprises at least one incision-opening-preventer structured and arranged to assist preventing the opening of at least one incision line wrapped by such at least one wrapper). Furthermore, in chest-wrap arrangement 105, medical dressing 103 preferably assists maintaining the comfort and mobility of patient 102. In chest-wrap arrangement 105, medical dressing 103 preferably does not interfere with the ability of patient 102 to breathe and make body movements. Furthermore, in chest-wrap arrangement 105, medical dressing 103 preferably allows patient 102 to rotate the shoulders or waist while preferably minimally disrupting the integrity of surgical incision lines, sutures, and stitches. In addition, in chest-wrap arrangement 105, medical dressing 103 preferably will not easily self-loosen, preferably even when employed on a persistent vertebrate animal. The manner in which bandage 120 is wrapped and secured around torso 110 in chest-wrap arrangement 105 according to wrapping technique 200 is described in greater detail below.

FIG. 2A shows a front view, illustrating bandage 120 of medical dressing 103, according the preferred embodiment of FIG. 1. Bandage 120 preferably comprises elastomeric properties, preferably enabling bandage 120 to be stretched and wrapped around a body part of patient 102, as shown in FIG. 1 (this arrangement at least herein embodying wherein such at least one wrapper further comprises at least one stretch-potential-provider structured and arranged to provide stretch potential to such at least one wrapper). In addition, the elastomeric properties of bandage 120 preferably minimally interfere with the physical mobility of patient 102. Furthermore, the elastomeric properties of bandage 120 preferably permit the breathing of patient 102 (this arrangement at least herein embodying wherein such at least one stretch-potential-provider is further structured and arranged to permit at least resting-state breathability to the at least one vertebrate life form, when such at least one wrapper is wrapped around at least one torso region of the at least one vertebrate life form). The elastomeric properties of bandage 120 preferably are provided by at least one elastomeric material. Such at least one elastomeric material preferably comprises at least one polyurethane-based elastomer, alternately preferably at least one polyester-based elastomer, alternately preferably at least one olefin-based elastomer, alternately preferably at least one polyamide-based elastomer, alternately preferably at least one vinyl-based elastomer. Upon reading this specification, those with ordinary skill in the art will now appreciate that, under appropriate circumstances, considering such issues as design preference, user preference, manufacturer preference, structural requirements, available materials, technological advances, etc., other elastomeric materials, such as, for example, other polymeric materials, other natural or synthetic materials, mixtures of elastomeric materials, etc., may suffice.

Bandage 120 preferably comprises sufficient strength to preferably provide sufficient force to a wound site in order to assist preventing the opening of sutures or incision lines wrapped by bandage 120. In addition, bandage 120 preferably comprises at least one hypoallergenic material for assisting minimizing any allergic response experienced by patient 102. In addition, bandage 120 preferably comprises at least one material to assist preventing bandage 120 from sticking to a wound site or the skin wrapped by bandage 120. Such at least one material may comprise, for example, at least one fluoropolymer coating such as Teflon®, or at least one silicone material.

Bandage 120 preferably is washable such that bandage 120 preferably can be reused. Furthermore, bandage 120 preferably is lightweight and non-cumbersome in order to preferably minimally interfere with the physical mobility of patient 102. Other preferred properties of bandage 120 will be described in further detail below. Upon reading this specification, those with ordinary skill in the art will now appreciate that, under appropriate circumstances, considering such issues as design preference, user preference, manufacturer preference, structural requirements, available materials, etc., other material arrangements, such as, for example, bandage materials with antimicrobial properties, biodegradable materials, disposable materials, etc., may suffice.

Bandage 120 preferably is secured in a desired wrapped arrangement, such as chest-wrap arrangement 105, using at least one fastening arrangement, preferably at least one hook and loop fastening arrangement. Alternately preferably, bandage 120 may comprise self-adhering properties for holding bandage 120 in such at least one fastening arrangement. Bandage 120 preferably comprises at least one first securing member 132 affixed on one end of bandage 120 and at least one second securing member 134 affixed on an opposite end of bandage 120, as shown. First securing member 132 preferably is oriented towards front side 133 of bandage 120, as shown. Second securing member 134 preferably is oriented towards the back side of bandage 120, as shown.

First securing member 132 and second securing member 134 preferably are capable of releasably adhering to bandage 120 to secure bandage 120 by at least one hook and loop fastening arrangement. In the above described securing arrangement, first securing member 132 and second securing member 134 preferably comprise hook fasteners and bandage 120 preferably comprises a loop fastener. Upon reading this specification, those with ordinary skill in the art will now appreciate that, under appropriate circumstances, considering such issues as design preference, user preference, user needs, structural requirements, available materials, technological advances, etc., other fastening arrangements, such as, for example, self-adhering materials, clips, clasps, adhesive tape, pins, other fasteners, other hook and loop fastening arrangements, etc., may suffice.

Bandage 120 preferably comprises a compact size, preferably enabling bandage 120 to be easily carried by patient 102, caretakers, health care professionals, emergency workers, athletes, or soldiers in a battlefield situation. Bandage 120 preferably comprises a length of from about thirty inches to about eighty inches, as shown by dimension B in FIG. 2A. Bandage 120 preferably comprises a width of from about three inches to about six inches, as shown by dimension A in FIG. 2A. More particularly, bandage 120 preferably is available in three, four, five, and six inch widths, as shown by dimension A. Upon reading this specification, those with ordinary skill in the art will now appreciate that, under appropriate circumstances, considering such issues as design preference, user preference, structural requirements, available materials, user size, wound type, wound site, etc., other bandage sizes, such as, for example, other lengths, other widths, etc., may suffice.

For a particular application, such as a particular wound-type and wound site, bandage 120 preferably requires less material (shorter length) than a typical compression bandage (such as an ACE bandage). Accordingly, bandage 120 preferably does not need to be wrapped as many times around a wound site as would be required by a typical compression bandage. Therefore, the force applied through compression in wrapping the wound site with bandage 120 will be less than the force exerted through compression in wrapping a wound site with a typical compression bandage. This reduced force preferably assists reducing the risk of damage to wound tissue and preferably assists reducing the risk of tissue necrosis or other factors that would hinder wound management and the healing process.

FIG. 2B shows a sectional view, through the section 2B-2B of FIG. 2A, according to the preferred embodiment of FIG. 1. Bandage 120 preferably comprises a plurality of layers 117, preferably three layers 117, as shown. Layers 117 preferably comprise at least one body layer 124, at least one inner layer 126, and at least one outer layer 128, as shown. Body layer 124, inner layer 126, and outer layer 128 preferably are in direct contact and preferably are united in bandage 120, as shown (this arrangement at least herein embodying wherein such at least one wrapper further comprises at least one uniter structured and arranged to unite such at least one exudate-transporter and such at least one exudate-absorber; and this arrangement at least herein embodying wherein such wrapper means comprises uniter means for uniting such exudate-transporter means and such exudate-absorber means). Upon reading this specification, those with ordinary skill in the art will now appreciate that, under appropriate circumstances, considering such issues as design preference, user preference, structural requirements, manufacture preference, available materials, wound type, wound site, etc., other bandage layer arrangements, such as, for example, more layers, fewer layers, etc., may suffice.

Body layer 124 and outer layer 128 preferably are made from the same material. In use, body layer 124 of bandage 120 preferably is in contact with the skin of patient 102. Alternately preferably, outer layer 128 of bandage 120 preferably contacts the skin of patient 102. Body layer 124 (at least herein embodying wherein such at least one wrapper comprises at least one exudate-transporter structured and arranged to transport at least one body exudate away from the at least one wound and at least one wound site surrounding the at least one wound; and at least herein embodying wherein such at least one exudate-transporter further comprises at least one perspiration-transporter structured and arranged to transport perspiration away from such at least one skin portion wrapped by such at least one wrapper; and at least herein embodying wherein such wrapper means comprises exudate-transporter means for transporting at least one body exudate away from the at least one wound and at least one wound site surrounding the at least one wound; and at least herein embodying wherein such at least one exudate-transporter comprises at least one flow-assistor structured and arranged to assist flow of such at least one body exudate away from the at least one wound and such at least one wound site) and outer layer 128 preferably comprise at least one material with wicking properties for removing or withdrawing water-based wound exudates and/or perspiration away from a wound site and/or for assisting delivering at least one healing agent to a wound site. The above described arrangement at least herein embodies wherein such exudate-transporter comprises at least one first-exudate transporter and at least one second-exudate transporter each structured and arranged to transport such at least one body exudate away from the at least one wound and such at least one wound site surrounding the at least one wound.

Materials with wicking properties, as described herein, refers to materials which are capable of transporting liquids, preferably water-based liquids, away from a wet surface in which they are in contact. Furthermore, materials with wicking properties, as described herein, preferably do not retain such water based-liquids unless saturated. Furthermore, body layer 124 and outer layer 128 preferably are comprised of at least one elastomeric material which preferably lends elasticity (stretch-ability) to body layer 124 and outer layer 128.

Suitable materials for body layer 124 and outer layer 128 may comprise, for example, polyamide-based materials, polyurethane materials, polyurethane foams, other foam-based dressings, polyester-based materials, or other natural or synthetic fibers. Upon reading this specification, those with ordinary skill in the art will now appreciate that, under appropriate circumstances, considering such issues as design preference, user preference, manufacturer preference, structural requirements, available materials, technological advances, etc., other materials with wicking properties, such as, for example, other natural or synthetic fibers, mixtures of materials with wicking properties, woven fabrics, etc., may suffice.

Body layer 124, if in contact with the skin of patient 102, preferably wicks wound exudates and/or perspiration away from the skin of patient 102 (this arrangement at least embodying herein at least one first unidirectional-flow-assistor structured and arranged to assist unidirectional flow of such at least one body exudate from the at least one wound to such at least one first exudate-transporter). Furthermore, body layer 124 preferably transports wound exudates and/or perspiration to inner layer 126 (this arrangement at least embodying herein at least one intermediate unidirectional-flow-assistor structured and arranged to assist unidirectional flow of such at least one body exudate from such at least one first exudate-transporter to such at least one exudate-absorber).

Inner layer 126 preferably comprises a material with stretch potential which preferably does not inhibit the ability of body layer 124 and outer layer 128 to stretch. In addition, inner layer 126 (at least herein embodying wherein such at least one wrapper further comprises at least one exudate-absorber structured and arranged to absorb such at least one body exudate transported away from the at least one wound and such at least one wound site by such at least one exudate-transporter; and at least herein embodying wherein such wrapper means comprises exudate-absorber means for absorbing such at least one body exudate transported away from the at least one wound and such at least one wound site by such exudate-transporter means) preferably is made from an absorbent material that is capable of collecting wound exudates and/or perspiration that are wicked away from the skin or wound site by body layer 124 (or outer layer 128). Absorbent materials, as described herein, refers to materials which have the property of absorbing liquids, preferably water-based liquids, and preferably have the capacity to retain such liquids until reaching saturation. Suitable materials for inner layer 126 preferably may comprise, for example, materials comprising cotton, gauze-like materials, alginate materials, polyester materials, hydrocolloid materials, cellulose-based materials, or materials comprising natural or synthetic absorbent polymers or fabrics. Upon reading this specification, those with ordinary skill in the art will now appreciate that, under appropriate circumstances, considering such issues as design preference, user preference, manufacturer preference, structural requirements, available materials, technological advances, etc., other material arrangements, such as, for example, cotton pads, other natural or synthetic materials, etc., may suffice.

As inner layer 126 reaches its capacity for storage of wound exudates and/or perspiration, excess wound exudates preferably are drawn away from inner layer 126 by the wicking action of outer layer 128 according to flow direction 118, as shown (this arrangement at least embodying herein at least one second unidirectional-flow-assistor structured and arranged to assist unidirectional flow of such at least one body exudate from such at least one exudate-absorber to such at least one second-exudate transporter). Wound exudates and perspiration collected by outer layer 128 preferably are transported to outer surface 125 of outer layer 128 according to flow direction 118, as shown (this arrangement at least embodying herein at least one third unidirectional-flow-assistor structured and arranged to assist unidirectional flow of such at least one body exudate from such at least one second exudate-transporter to at least one outer surface of such at least one wrapper). Alternately preferably, an additional absorbent layer may be introduced over outer layer 128 in order to collect wound exudates and to prevent the spilling of wound exudates out of bandage 120.

The accumulation of wound exudates and/or perspiration on outer surface 125 of outer layer 128 preferably is detectable by the naked-eye, signaling to patient 102 or to at least one caretaker of patient 102 to replace bandage 120 (this arrangement at least herein embodying wherein such at least one wrapper further comprises at least one exudate-accumulation-indicator structured and arranged to indicate accumulation of such at least one body exudate on at least one outer surface of such at least one wrapper). In addition, such accumulation of wound exudates and/or perspiration on outer surface 125 of outer layer 128 preferably allows patient 102 or at least one caretaker to identify conditions which cause normal hemodynamic parameters to be compromised, such as hemorrhaging or infections, which may otherwise be undetectable when masked by a medical dressing or bandage (this arrangement at least herein embodying wherein such at least one exudate-accumulation-indicator comprises at least one hemorrhage-indicator structured and arranged to indicate hemorrhaging of such at least one vertebrate life form). This arrangement preferably allows for quicker medical intervention in such situations.

FIG. 2C shows a sectional view, through the section 2C-2C of FIG. 2A, illustrating the dispersion of at least one chemical alert substance 130 throughout bandage 120, according to an alternately preferred embodiment of the present invention. Chemical alert substance 130 preferably is used with medical dressing 103 preferably at least when quick alert of healing problems is critical, such as during post-operative conditions. Chemical alert substance 130 preferably identifies the type of wound exudates being wicked away from a wound site and absorbed by bandage 120. Chemical alert substance 130 (at least embodying herein at least one exudate-identifier structured and arranged to identify such at least one body exudate as at least one body exudate species) preferably assists to identify wound exudates as at least one of the following: blood; gastric fluids; serous fluids; purulent fluids; lymph fluids; or, other bodily waste products.

Chemical alert substance 130 (at least embodying herein at least one detectable-signal-generator structured and arranged to generate at least one detectable signal in response to such at least one body exudate) preferably comprises chemical identifiers that respond to one or more exudates such as, for example, blood, gastric fluids, serous fluids, purulent fluids, lymph fluids, or other biological waste products with at least one detectable signal. Such at least one detectable signal preferably comprises at least one color change, alternately preferably at least one visual indication detectable by the naked-eye, alternately preferably at least one fluorescence change. Chemical alert substance 130 preferably responds to each of the above described wound exudates by displaying such at least one detectable signal, preferably at least one distinct detectable signal for each of the above-described wound exudates (this arrangement at least herein embodying wherein such at least one exudate-identifier comprises at least one distinct-signal-generator structured and arranged to generate at least one distinct such at least one detectable signal correlated with such at least one body exudate species). This arrangement preferably allows patient 102 or a caretaker of patient 102 to identify the type(s) of wound exudates being released based on the resulting color change or other visual indication observed on bandage 120. Upon reading this specification, those with ordinary skill in the art will now appreciate that, under appropriate circumstances, considering such issues as design preference, user preference, manufacturer preference, structural requirements, available materials, wound type, wound site, technological advances, etc., other detecting arrangements for detection of wound exudates, such as, for example, texture changes, electrical signals, heat signals, etc., may suffice.

Chemical alert substance 130 preferably is evenly dispersed throughout bandage 120, as shown in FIG. 2C. Alternately preferably, chemical alert substance 130 preferably comprises at least one coating on at least one outer surface 125 of bandage 120. Alternately preferably, chemical alert substance 130 preferably is localized in a single layer 117 of bandage 120. Alternately preferably, chemical alert substance 130 preferably is localized in at least one portion of at least one layer 117 of bandage 120.

Chemical alert substance 130 preferably comprises a non-toxic substance which does not disturb any of the preferred properties of bandage 120 described herein, such as, elasticity, absorbent properties, wicking properties, or hypoallergenic properties. Chemical alert substance 130 preferably comprises at least one liquid, gel, or solid chemical capable of displaying at least one detectable signal in response to the various types of wound exudates described above. Suitable substances for chemical alert substance 130, may comprise, for example, phenolthalein, luminol, or a chemical alert substance sold under the trademark Blue-Star® Forensic. Upon reading this specification, those with ordinary skill in the art will now appreciate that, under appropriate circumstances, considering such issues as design preference, user preference, manufacturer preference, structural requirements, available materials, technological advances, etc., other natural or synthetic chemicals, non-toxic chromophores, non-toxic fluorophores, etc., may suffice.

FIG. 3A shows a front view, illustrating pocket 140 of medical dressing 103, according to the preferred embodiment of FIG. 1. FIG. 3B shows a rear view, illustrating pocket 140 of medical dressing 103, according the preferred embodiment of FIG. 1. Pocket 140 preferably is structured and arranged to contain at least one surgical drain assembly 160, as shown FIG. 1 and as discussed above. Alternately preferably, pocket 140 preferably is structured and arranged to contain at least one other medical care item, as discussed above. Pocket 140 preferably is releasably attached to bandage 120. Pocket 140 preferably is attached at a user-selectable position of bandage 120. Pocket 140 preferably comprises sealed edges 146 and at least one opening 150, as shown. Opening 150 preferably provides a passage to pocket portion 148, as shown. Opening 150 preferably provides access to the interior of pocket portion 148, as shown.

The geometry of pocket 140 preferably is square, alternately preferably rectangular, alternately preferably round, alternately preferably circular. Pocket 140 preferably comprises dimensions capable of containing drain 162 of surgical drain assembly 160 (see FIG. 1) or at least one healing agent. Upon reading this specification, those with ordinary skill in the art will now appreciate that, under appropriate circumstances, considering such issues as design preference, user preference, manufacturer preference, structural requirements, available materials, technological advances, etc., other pocket dimension arrangements, such as, for example, other dimensions capable of containing other medical care items, etc., may suffice.

Pocket 140 preferably is comprised of at least one hand-washable or machine-washable material. Pocket 140 preferably is comprised of the same material as bandage 120. Upon reading this specification, those with ordinary skill in the art will now appreciate that, under appropriate circumstances, considering such issues as design preference, user preference, manufacturer preference, structural requirements, available materials, technological advances, etc., other material arrangements, such as, for example, other natural or synthetic materials, disposable materials, biodegradable materials, etc., may suffice.

Pocket 140 preferably comprises at least one securing strip 152 (at least herein embodying wherein such at least one container comprises at least one third fastener structured and arranged to fasten such at least one container to such at least one wrapper at at least one user-selected location), preferably two securing strips 152, as shown. Securing strips 152 preferably are located on at least one back side 144 of pocket 140, as shown in FIG. 3B. Alternately preferably, securing strips 152 are located around the perimeter of backside 144. Upon reading this specification, those with ordinary skill in the art will now appreciate that, under appropriate circumstances, considering such issues as design preference, user preference, manufacturer preference, structural requirements, available materials, etc., other securing strip arrangements, such as, for example, more than two securing strips, placement of a single securing strip in the center of the pocket, multiple securing strips, etc., may suffice.

Securing strips 152 preferably are structured and arranged to secure pocket 140 to bandage 120, as shown in FIG. 1 and FIG. 3C. Securing strips 152 preferably comprise at least one material capable of mating with at least one outer surface 125 of bandage 120. More particularly, securing strips 152 preferably function as a hook material capable of mating with a loop material of such at least one outer surface 125 of bandage 120. Alternately preferably, securing strips 152 preferably function as a loop material capable of mating with a hook material of outer layer 128 of bandage 120. Upon reading this specification, those with ordinary skill in the art will now appreciate that, under appropriate circumstances, considering such issues as design preference, user preference, user needs, structural requirements, available materials, technological advances, etc., other fastening arrangements, such as, for example, clips, clasps, adhesive tape, pins, incorporation of hook and loop fasteners on bandage 120, other fasteners, etc., may suffice.

FIG. 3C shows a sectional view, through the section 3C-3C of FIG. 3A, illustrating attachment of pocket 140 to bandage 120 with securing strips 152, according the preferred embodiment of FIG. 1. In FIG. 3C, pocket 140 is shown supporting surgical drain assembly 160. Pocket 140 preferably supports drain 162 of surgical drain assembly 160, with drain tubing 164 preferably projecting from pocket portion 148 through opening 150, as shown. Drain 162 preferably is supported in pocket portion 148 of pocket 140, as shown. Pocket 140 preferably is attached to outer surface 125 of bandage 120 using securing strips 152, as shown.

FIG. 4A shows a front view, illustrating first wrapping step 202 of wrapping technique 200 of medical dressing systems 100, according to the preferred embodiment of the present invention. FIG. 4B shows a rear view, illustrating first wrapping step 202 of wrapping technique 200 of medical dressing systems 100, according the preferred embodiment of FIG. 1. Wrapping technique 200 is preferably accomplished by at least one caretaker of patient 102, alternately preferably by patient 102. Wrapping technique 200 preferably comprises a specific technique for wrapping bandage 120 radially with respect to central axis X preferably running vertically through the center of patient 102, as shown. Wrapping technique 200 preferably is adapted for wrapping bandage 120 around torso 110 of patient 102 to form chest-wrap arrangement 105, as shown in FIG. 1. The resulting chest-wrap arrangement 105 preferably provides wound management, preferably post-mastectomy wound management. The benefits of chest-wrap arrangement 105 for post-mastectomy wound management have been described in detail above. Upon reading this specification, those with ordinary skill in the art will now appreciate that, under appropriate circumstances, considering such issues as user preference, user needs, etc., other types of wounds, such as, for example, other post-operative surgical wounds, post-operative cosmetic surgery wounds, sports injuries, bone injuries, muscle injuries, burns, inflammations, etc., may suffice. Upon reading this specification, those with ordinary skill in the art will now appreciate that, under appropriate circumstances, considering such issues as design preference, user preference, user needs, structural requirements, available materials, etc., other wrapping techniques may suffice.

First wrapping step 202 preferably is accomplished by firmly wrapping bandage 120 over lower abdominal region 151 of patient 102, as shown in FIG. 4A and FIG. 4B. Such firm wrapping of bandage 120 preferably comprises applying sufficient external force to maintain the integrity of sutures or incision lines, while preferably minimally interfering with the comfort, mobility, blood circulation, and breathability of patient 102.

First wrapping step 202 preferably commences by approximately aligning at least one loose end 175 of bandage 120 preferably along start edge 104 located on ventral side 172 of patient 102, as shown in FIG. 4A (this arrangement at least embodying herein placing at least one first terminal edge of the at least one medical dressing above at least one umbilicus area located on at least one abdominal region of the at least one vertebrate life form; and this arrangement at least embodying herein aligning such at least one first terminal edge of the at least one medical dressing parallel to at least one vertical axis running parallel to at least one sagittal plane running vertically through the center of the at least one vertebrate life form). Start edge 104 preferably is located above umbilicus area 176 and preferably lies parallel to central axis X, as shown. Bandage 120 preferably is wrapped around lower abdominal region 151 with first securing member 132 oriented away from patient 102 and not in contact with the skin of patient 102, as shown. Upon reading this specification, those with ordinary skill in the art will now appreciate that, under appropriate circumstances, considering such issues as design preference, user preference, user needs, wound site, wound type, patient body type, etc., other starting locations for wrapping technique 200 may suffice.

First wrapping step 202 preferably further comprises continuing firmly wrapping bandage 120, radially with respect to central axis X, approximately horizontally across lower abdominal region 151 according to first wrapping direction 106, as shown (this arrangement at least embodying herein firmly wrapping the at least one medical dressing, radially with respect to such at least one vertical axis, horizontally across such at least one abdominal region and toward at least one dorsal side of the at least one torso region; and this arrangement at least embodying herein firmly wrapping the at least one medical dressing, radially with respect to such at least one vertical axis, horizontally across at least one the first body section). First wrapping step 202 preferably further comprises continuing wrapping bandage 120, radially with respect to central axis X, preferably horizontally across lower back 180 located on dorsal side 174 of patient 102, as shown in FIG. 4B (this arrangement at least embodying herein continuing firmly wrapping the at least one medical dressing, radially with respect to such at least one vertical axis, horizontally across at least one lower back region and towards at least one ventral side of the at least one torso region; and this arrangement at least embodying herein continuing firmly wrapping the at least one medical dressing, radially with respect to such at least one vertical axis, horizontally across the at least one second body section).

First wrapping step 202 preferably further comprises continuing firmly wrapping bandage 120, radially with respect to central axis X, preferably horizontally across lower abdominal region 151, preferably creating at least one complete turn of bandage 120 around lower torso 153 of patient 102, as shown in FIG. 4A (this arrangement at least embodying herein continuing firmly wrapping the at least one medical dressing, radially with respect to such at least one vertical axis, horizontally across such at least one abdominal region, completing at least one complete turn of the at least one medical dressing around at least one lower torso region of the at least one vertebrate life form; and this arrangement at least embodying herein continuing firmly wrapping the at least one medical dressing, radially with respect to such at least one vertical axis, horizontally across such at least one first body section, creating at least one complete turn around the at least one body part). Bandage 120 preferably is secured with first securing member 132 (at least herein embodying wherein such at least one fastener comprises at least one first fastener structured and arranged to fasten such at least one wrapper in at least one intermediate wrapped arrangement) (or second securing member 134) at first fastening position 170, as shown.

According to first wrapping step 202, bandage 120 preferably is fastened at first fastening position 170 using at least one hook and loop mating arrangement, wherein first securing member 132 preferably functions as a hook fastener and bandage 120 preferably functions as a loop fastener (this arrangement at least embodying herein fastening the at least one medical dressing, with at least one first fastener, at at least one first fastening position situate about such at least one first terminal edge; and this arrangement at least embodying herein fastening the at least one medical dressing at at least one first fastening position, situate about above such at least one umbilicus area, with at least one first fastener). First fastening position 170 preferably is located approximately along start edge 104 above umbilicus area 176, as shown. Upon reading this specification, those with ordinary skill in the art will now appreciate that, under appropriate circumstances, considering such issues as design preference, user preference, user needs, structural requirements, available materials, technological advances, etc., other fastening arrangements, such as, for example, clips, clasps, adhesive tape, pins, other hook and loop fastening arrangements, other fasteners, etc., may suffice.

FIG. 5A shows a front view, illustrating second wrapping step 204 of wrapping technique 200, according to the preferred embodiment of FIG. 1. FIG. 5B shows a rear view, illustrating second wrapping step 204 of wrapping technique 200, according to the preferred embodiment of FIG. 1. Second wrapping step 204 preferably follows first wrapping step 202 (see FIG. 4A and FIG. 4B). Second wrapping step 204 preferably comprises continuing firmly wrapping bandage 120 from first fastening position 170 around torso 110 of patient 102, radially with respect to central axis X, as shown. Second wrapping step 204 preferably comprises wrapping bandage 120 upward from first fastening position 170 at angle Q1 over left breast area 178 according to second wrapping direction 108, as shown. Angle Q1 preferably slopes upward (relative to horizontal) toward the left (from the point of view of patient 102) at an angle of between about forty degrees to about fifty degrees, preferably forty-five degrees, as shown (this arrangement at least embodying herein continuing firmly wrapping the at least one medical dressing, radially with respect to such at least one vertical axis, upward at an angle of from about forty degrees to about fifty degrees from such at least one first fastening position across the at least one first body section). Upon reading this specification, those with ordinary skill in the art will now appreciate that, under appropriate circumstances, considering such issues as design preference, user preference, user needs, wound type, wound site, patient body type, etc., other bandage wrapping arrangements, such as, for example, other angles, wrapping in the opposite direction, etc., may suffice.

Second wrapping step 204 preferably further comprises continuing firmly wrapping bandage 120 under left arm 182 and below left axilla 184, as shown. Second wrapping step 204 preferably further comprises continuing firmly wrapping bandage 120, radially with respect to central axis X, horizontally across upper back 186 located on dorsal side 174, according to second wrapping direction 108, as shown in FIG. 5B (this arrangement at least embodying herein continuing firmly wrapping the at least one medical dressing, radially with respect to such at least one vertical axis, horizontally across the at least one second body section). Upon reading this specification, those with ordinary skill in the art will now appreciate that, under appropriate circumstances, considering such issues as design preference, user preference, user needs, wound type, wound site, patient body type, etc., other bandage wrapping arrangements, such as, for example, wrapping across other regions of the back, wrapping in the opposite direction, etc., may suffice.

Second wrapping step 204 preferably further comprises continuing firmly wrapping bandage 120, radially with respect to central axis X, under right arm 188, below right axilla 190, and toward ventral side 172 of torso 110, according to second wrapping direction 108, as shown in FIG. 5A.

FIG. 6A shows a front view, illustrating third wrapping step 206 of wrapping technique 200, according to the preferred embodiment of FIG. 1. FIG. 6B shows a rear view, illustrating third wrapping step 206 of wrapping technique 200, according to the preferred embodiment of FIG. 1. Third wrapping step 206 preferably follows second wrapping step 204 (see FIG. 5A and FIG. 5B). Third wrapping step 206 preferably comprises continuing firmly wrapping bandage 120 around torso 110 of patient 102, radially with respect to central axis X, as shown. Third wrapping step 206 preferably comprises continuing wrapping bandage 120 downward (relative to horizontal) from under right axilla 190 at an angle of between about thirty degrees to about fifty degrees across ventral side 172 and over right breast area 192, according to third wrapping direction 109, as shown (this arrangement at least embodying herein continuing firmly wrapping the at least one medical dressing, radially with respect to such at least one vertical axis, downward at an angle of from about thirty degrees to about fifty degrees across the at least one first body section).

Once bandage 120 preferably has approximately reached transverse plane 115, bandage 120 preferably is wrapped horizontally across middle back 194 of dorsal side 174, according to third wrapping direction 109, as best shown in FIG. 6B (this arrangement at least embodying herein continuing firmly wrapping the at least one medical dressing, radially with respect to such at least one vertical axis, horizontally across the at least one second body section). Following such wrapping of bandage 120 across middle back 194, third wrapping step 206 preferably further comprises wrapping bandage 120 under right arm 188 towards ventral side 172, according to third wrapping direction 109, as shown in FIG. 6A and FIG. 6B. Upon reading this specification, those with ordinary skill in the art will now appreciate that, under appropriate circumstances, considering such issues as design preference, user preference, user needs, wound type, wound site, patient body type, etc., other bandage wrapping arrangements, such as, for example, other wrapping angles, wrapping across other regions of the back, wrapping in the opposite direction, etc., may suffice.

After completion of first wrapping step 202, second wrapping step 204, and third wrapping step 206 according to the steps illustrated in FIG. 4A through FIG. 6B, lower back 180, middle back 194, and upper back 186 preferably will have each been covered by one at least one layer of bandage 120, as best shown in FIG. 6B.

FIG. 7A shows a front view, illustrating fourth wrapping step 208 of wrapping technique 200, according to the preferred embodiment of FIG. 1. FIG. 7B shows a rear view, illustrating fourth wrapping step 208 of wrapping technique 200, according to the preferred embodiment of FIG. 1. Fourth wrapping step 208 preferably follows third wrapping step 206 (see FIG. 6A and FIG. 6B). Fourth wrapping step 208 preferably comprises continuing firmly wrapping bandage 120 around torso 110 of patient 102, radially with respect to central axis X, as shown. Fourth wrapping step 208 preferably comprises wrapping bandage 120 upward across ventral side 172 at an angle Q3 according to fourth wrapping direction 111, as shown (this arrangement at least embodying herein continuing firmly wrapping the at least one medical dressing, radially with respect to such at least one vertical axis, upward at an angle of from about forty degrees to about fifty degrees across the at least one first body section). During such wrapping, bandage 120 preferably is wrapped under right breast area 192, across left breast area 178, and under left axilla 184, as shown. Angle Q3 preferably slopes upward (from horizontal) toward the left (from the point of view of patient 102) at an angle of between about thirty degrees to about fifty degrees, preferably forty-five degrees, as shown in FIG. 7A. Upon reading this specification, those with ordinary skill in the art will now appreciate that, under appropriate circumstances, considering such issues as design preference, user preference, user needs, wound type, wound site, patient body type, etc., other bandage wrapping arrangements, such as, for example, other wrapping angles, wrapping in a the opposing direction, etc., may suffice.

Following the wrapping steps illustrated in FIG. 7A, fourth wrapping step 208 preferably further comprises continuing firmly wrapping bandage 120 preferably horizontally across at least a portion of upper back 186 according to fourth wrapping direction 111, as shown in FIG. 7B (this arrangement at least embodying herein continuing firmly wrapping the at least on medical dressing, radially with respect to such at least one vertical axis, horizontally across the at least one second body section). Upon reading this specification, those with ordinary skill in the art will now appreciate that, under appropriate circumstances, considering such issues as design preference, user preference, user needs, wound type, wound site, patient body type, etc., other bandage wrapping arrangements, such as, for example, wrapping other regions of the back, wrapping the opposing direction, etc., may suffice.

After completion of forth wrapping step 208, at least a portion of upper back 186 preferably is covered by at least two layers of bandage 120, as shown.

FIG. 8A shows a front view, illustrating fifth wrapping step 210 of wrapping technique 200, according the preferred embodiment of FIG. 1. FIG. 8B shows a rear view, illustrating fifth wrapping step 210 of wrapping technique 200, according to the preferred embodiment of FIG. 1. Fifth wrapping step 210 preferably follows fourth wrapping step 208 (see FIG. 7A and FIG. 7B). Fifth wrapping step 210 preferably comprises continuing firmly wrapping bandage 208 around torso 110 of patient 102, radially with respect to central axis X, as shown. Fifth wrapping step 210 preferably comprises wrapping bandage 120 downward (relative to horizontal) from under right axilla 190 at an angle of between about thirty degrees to about fifty degrees across ventral side 172, according to fifth wrapping direction 113, as shown (this arrangement at least embodying herein continuing firmly wrapping the at least one medical dressing, radially with respect to such at least one vertical axis, downward at an angle of from about thirty degrees to about fifty degrees across the at least one first body section). During such wrapping, bandage 120 preferably is wrapped over right breast area 192 until preferably reaching approximately transverse plane 115, as shown. Upon reading this specification, those with ordinary skill in the art will now appreciate that, under appropriate circumstances, considering such issues as design preference, user preference, user needs, wound type, wound site, patient body type, etc., other bandage wrapping arrangements, such as, for example, other wrapping angles, other termination points, wrapping in the opposite direction, etc., may suffice.

According to fifth wrapping step 210, bandage 120 preferably is further wrapped toward dorsal side 174 of patient 102, as shown in FIG. 8B. Upon reaching transverse plane 115, or upon reaching at least one termination point 127 of bandage 120, bandage 120 preferably is secured in position using second securing member 134 (at least embodying herein at least one fastener structured and arranged to fasten such at least one wrapper in at least one wrapped arrangement; and at least herein embodying wherein such at least one fastener further comprises at least one second fastener structured and arranged to fasten such at least one wrapper in at least one final wrapped arrangement) (or first securing member 132). The above described arrangement at least embodies herein fastening at least one second terminal edge of the at least one medical dressing with at least one second fastener on the at least one wrapped arrangement.

Bandage 120 preferably is secured in position using at least one hook and loop mating arrangement, wherein second securing member 134 preferably functions as a hook fastener and bandage 120 preferably functions as a loop fastener. Upon reading this specification, those with ordinary skill in the art will now appreciate that, under appropriate circumstances, considering such issues as design preference, user preference, user needs, structural requirements, available materials, technological advances, etc., other fastening arrangements, such as, for example, clips, clasps, adhesive tape, pins, other hook and loop fastening arrangements, other hook and loop fastening arrangements, other fasteners, etc., may suffice.

Depending on the actual dimensions of torso 110 of patient 102 and the actual length of bandage 120, bandage 120 may be too short to fully complete fifth wrapping step 210 such that bandage 120 must be secured with second securing member 134 on ventral side 172 of patient 102. Alternatively, after completing fifth wrapping step 210, bandage 120 may be in excess such that bandage 120 must be secured with second securing member 134 on dorsal side 174 or further wrapped around patient 102 until reaching termination point 127, at which point bandage 120 preferably is secured with second securing member 134. The completion of fifth wrapping step 210 preferably generates chest-wrap arrangement 105, as shown.

Although wrapping technique 200 is described and illustrated in FIG. 4A through FIG. 8B by wrapping bandage 120 in a counterclockwise direction around torso 110 of patient 102 (when viewed from above patient 102), wrapping technique 200 preferably may also be effective if wrapping is performed in the opposite orientation or a clockwise direction around torso 110 (when viewed from above patient 102). Depending on the wound site, wound type, and body type of patient 102, wrapping technique 200 may be more effective for wound management by wrapping bandage 120 around torso 110 in a counterclockwise direction or by wrapping bandage 120 around torso 110 in a clockwise direction. Upon reading this specification, those with ordinary skill in the art will now appreciate that, under appropriate circumstances, considering such issues as design preference, user preference, user needs, wound type, wound site, etc., other variations of wrapping technique 200, such as, for example, other wrapping angles, other termination points, repeating multiple cycles of each of the above described illustrated wrapping steps, performing fewer than all of the above described and illustrated wrapping steps, adapting wrapping technique 200 for other regions of the body, incorporating wrapping steps to introduce appendage sleeves, circular wrapping methods, incorporating wrapping steps to wrap limbs, incorporating wrapping steps to wrap the neck, etc., may suffice.

Figure 9:
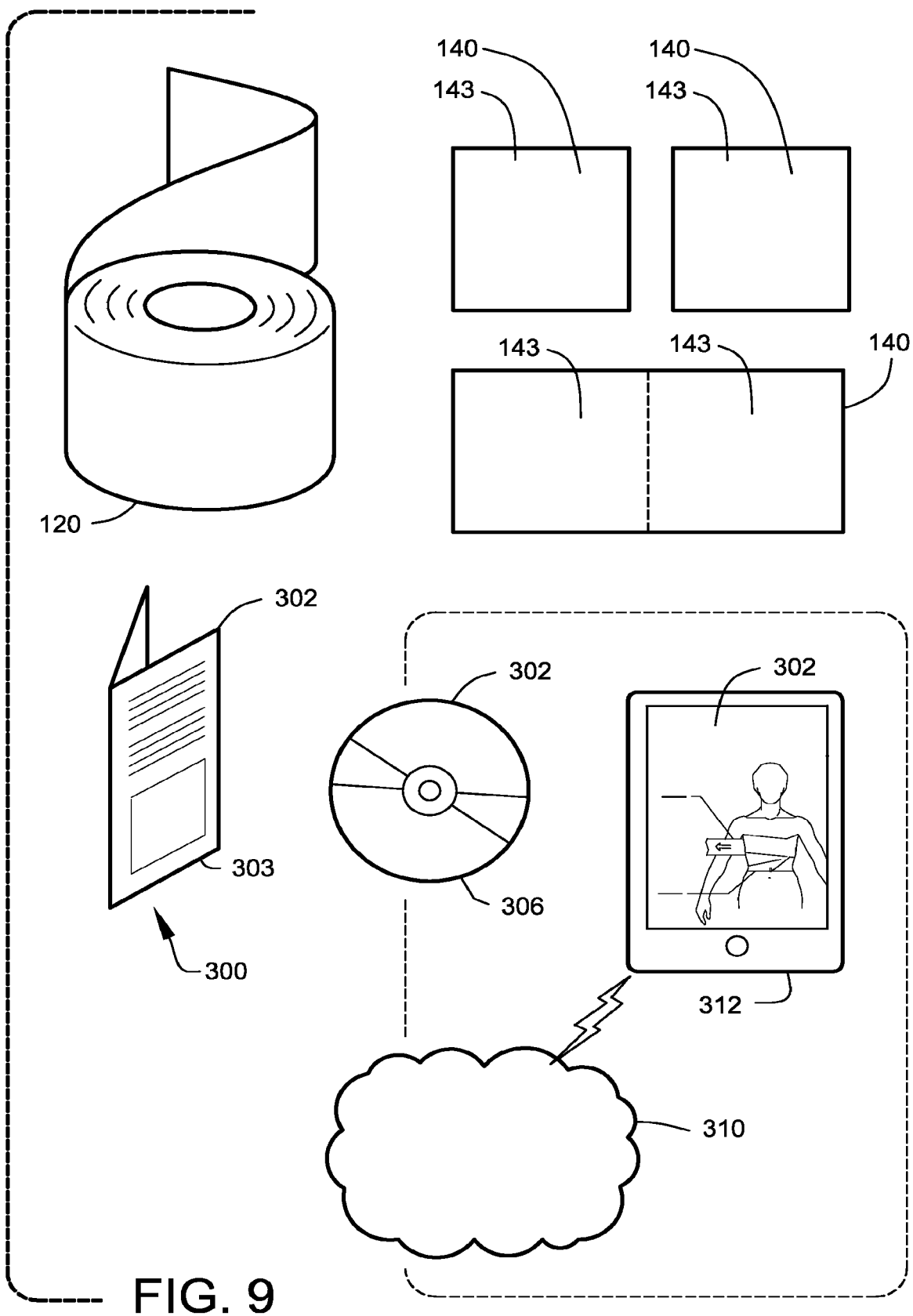
FIG. 9 shows perspective views, illustrating a wound management kit of medical dressing systems, according the preferred embodiment of FIG. 1.

FIG. 9 shows perspective views, illustrating wound management kit 300 of medical dressing systems 100, according the preferred embodiment of FIG. 1. Wound management kit 300 preferably comprises a kit for wound management and instructions for use. Wound management kit 300 preferably comprises at least one bandage 120 preferably wrapped in at least one compact arrangement, as shown. Wound management kit 300 preferably further comprises at least one pocket 140, alternately preferably at least one plurality of pockets 140, as shown. Each pocket 140 in wound management kit 300 preferably comprises at least one compartment 143 preferably structured and arranged to store at least one surgical drain assembly 160 (see FIG. 1 and FIG. 9) or at least one other medical care item. Alternately preferably, each pocket 140 comprises at least one plurality of compartments 143, as shown. Pockets 140 preferably are structured and arranged to fasten to any user-selected position of bandage 120, as shown in FIG. 1 and FIG. 3C.

Wound management kit 300 preferably further comprises at least one instruction manual 302 (at least embodying herein at least one instruction set providing at least one set of instructions for using such at least one medical dressing), as shown. Instruction manual 302 preferably comprises information and instruction for use of medical dressing system 100 for patient 102, healthcare professionals, caretakers, and/or any individual requiring wound management assistance. Instruction manual 302 preferably further comprises instructions for wrapping wounds, preferably comprising wrapping technique 200 (see FIG. 4A through FIG. 8B), and/or other suitable wound wrapping techniques which may vary depending on the wound type, wound location, and the body type of patient 102. Instruction manual 302 preferably comprises at least on paper booklet 303, alternately preferably at least one digital media 306, as shown. Digital media 306 preferably comprises at least one audio-file, alternatively preferably at least one video file, alternately preferably at least one audio-video file. Digital media 306 preferably comprises at least one compact-disc (CD) or at least one digital video disc (DVD). Alternately preferably, instruction manual 302 is located on at least one website accessible through internet 310 by at least one internet-enabled device 312, as shown. Upon reading this specification, those with ordinary skill in the art will now appreciate that, under appropriate circumstances, considering such issues as design preference, user preference, user needs, manufacturer preference, technological advances, etc., other instruction arrangements, such as, for example, instructions stored on a Universal Serial Bus (USB) drive, mobile device readable files, other digital files, etc., may suffice.

Although applicant has described applicant's preferred embodiments of this invention, it will be understood that the broadest scope of this invention includes modifications, such as, diverse shapes, sizes, colors, designs, and materials. Such scope is limited only by the below claims as read in connection with the above specification. Further, many other advantages of applicant's invention will be apparent to those skilled in the art from the above descriptions and the below claims.

What is claimed is:

1. A bandage configured to transport body exudate away from at least one wound located on at least one body part of at least one vertebrate life form, the bandage comprising:
opposite outside first and second sides, the bandage structured and being capable of being arranged to wrap the at least one body part with the first side of the bandage against the at least one body part;
the bandage comprising an outer first layer on the first side of the bandage, an outer second layer on the second side of the bandage, and an inner third layer being disposed between the first and second layers, the bandage further comprising at least one uniter permanently uniting the inner third layer with the outer first layer and permanently uniting the inner third layer with the outer second layer, the inner third layer being permanently united with both the outer first layer and with the outer second layer prior to the bandage being arranged to wrap the at least one wound and the at least one body part whereby the bandage is a unitary member;
the outer first layer comprising an outer side on the first side of the bandage and an inner side adjacent the inner third layer, the outer and inner sides of the outer first layer being separated by a thickness of the outer first layer, the outer first layer comprising a wicking material extending from the outer side to the inner side of the outer first layer, the wicking material of the outer first layer being of a type that does not retain water based-liquids unless saturated and being capable of transporting liquid in contact with the outer side of the outer first layer through the thickness of the outer first layer and to the inner side of the outer first layer;
the outer second layer comprising an outer side on the second side of the bandage and an inner side adjacent the inner third layer, the outer and inner sides of the outer second layer being separated by a thickness of the outer second layer, the outer second layer comprising a wicking material extending from the inner side to the outer side of the outer second layer, the wicking material of the outer second layer being of a type that does not retain water based-liquids unless saturated and being capable of transporting liquid in contact with the inner side of the outer second layer through the thickness of the outer second layer and to the outer side of the outer second layer; and
the inner third layer comprising opposite first and second sides separated by a thickness of the inner third layer, the first side of the inner third layer being adjacent the inner side of the outer first layer and the second side of the inner third layer being adjacent the inner side of the outer second layer, the inner third layer comprising an absorbent material being capable of absorbing water-based liquids and retaining the absorbed liquid until reaching saturation, the absorbent material extending from the first side to the second side of the inner third layer, the absorbent material on the first side of the inner third layer being against the inner side of the outer first layer and the absorbent material on the second side of the inner third layer being against the inner side of the outer second layer, the wicking material of the outer first layer and the wicking material of the outer second layer being a different material than the absorbent material of the inner third layer;
wherein the outer first layer, the outer second layer, and the inner third layer are permanently united to form a single roll;
wherein when the bandage is wrapping the at least one wound and the at least one body part with the outer side of the outer first layer of the bandage in contact with the wound, the outer first layer is configured to transport body exudate away from the at least one wound and from at least one wound site surrounding the at least one wound to the inner third layer, and when the absorbent material in the inner third layer becomes saturated with body exudate, the outer second layer transports body exudate away from the inner third layer to the outer side of the outer second layer;

wherein the bandage extends along a length, the bandage being elastically stretchable along the length of the bandage, wherein the bandage further comprises at least one elastomeric material selected from the group consisting of an olefin-based elastomer, a polyamide-based elastomer, a vinyl-based elastomer, and a mixture thereof;

wherein the wicking material of one or both of the outer first layer and the outer second layer of the bandage comprises at least one of the following materials: a polyamide-based material, a polyurethane material, a polyurethane foam material, a polyester-based material, a synthetic fiber material, and a natural fiber material;

wherein the bandage further comprises at least one healing agent being disposed on one or both of the outside first and second sides of the bandage, wherein the healing agent is an antibacterial or antimicrobial.

2. The bandage of claim 1, further comprising at least one detectable-signal-generator structured and arranged to generate at least one detectable signal in response to body exudate being in contact with the bandage.

3. The bandage of claim 2, wherein the at least one detectable signal is detectable by the naked eye.

4. The bandage of claim 3, wherein the at least one detectable signal comprises at least one color change.

5. The bandage of claim 1, wherein the inner third layer of the bandage consists solely of absorbent material.

6. The bandage of claim 5, wherein the absorbent material is at least one selected from the group consisting of cotton, gauze-like materials, alginate materials, polyester materials, hydrocolloid materials, cellulose-based materials, and materials comprising natural or synthetic absorbent polymers or fabrics.

7. The bandage of claim 1, further comprising a coating on the outer side of the outer first layer of the bandage, the coating capable of resisting adhesion of the bandage to the body part when the outer side of the outer first layer is against the body part.

8. The bandage of claim 7, wherein the coating comprises a skin-adhesion preventer.

9. The bandage of claim 1, wherein when the outer side of the outer first layer is in contact with the wound, the wicking material of the outer first layer is configured to transport body exudate away from the wound to the inner third layer of the bandage, and when the absorbent material in the inner third layer becomes saturated with body exudate, the wicking material of the outer second layer transports body exudate away from the inner third layer to the outer side of the outer second layer.

10. The bandage of claim 9, wherein body exudate transported by the wicking material of the outer second layer to the outer side of the outer second layer is detectable by the naked eye.

11. The bandage of claim 1, in combination with a pocket attached to or attachable to the bandage.

12. The bandage of claim 11, wherein one or both of the bandage and the pocket comprises one or more attachment members that releasably attach the pocket to the bandage.

13. The bandage of claim 1, wherein the bandage comprises torso-wrapability.

14. The bandage of claim 1, wherein the same type of wicking material is used for both the outer first layer and the outer second layer.

15. The bandage of claim 1, wherein one or both of the outer first layer and the outer second layer of the bandage consists solely of wicking material.

16. The bandage of claim 1, wherein the wicking material of the outer first layer is capable of transporting perspiration in contact with the outer side of the first outer layer.

17. The bandage of claim 1, wherein when the bandage is elastically stretched from a relaxed state to generate a force urging the bandage back to the relaxed state, and the stretched bandage is placed against a body part having a suture, the force compresses the suture.

18. The bandage of claim 1, wherein the wicking material of the outer first layer is configured to generate unidirectional flow of exudate towards the inner third layer when the outer first layer is transporting exudate away from the at least one wound.

19. The bandage of claim 1, wherein the wicking material of the outer second layer generates unidirectional flow of exudate towards the outer side of the outer second layer when the outer second layer is transporting exudate away from the inner third layer.

20. The bandage of claim 1, configured for being wrapped about the body part and being disposed in a wrapping arrangement, at least one fastener attached to the bandage and resisting unwrapping of the bandage, each at least one fastener being selected from the following: a hook and loop fastener, a clip, a clasp, an adhesive tape, and a pin.

21. The bandage of claim 1, wherein the bandage is washable and reusable.

* * * * *